| United States Patent [19] | [11] Patent Number: 4,816,462 |
| Nowicky | [45] Date of Patent: Mar. 28, 1989 |

[54] METHOD FOR DIAGNOSING AND FOR THE THERAPEUTIC TREATMENT OF TUMORS AND/OR INFECTIOUS DISEASES OF DIFFERENT TYPES WITH ALKALOID-COMPOUNDS

[76] Inventor: Wassyl Nowicky, Laimgrubengasse 19/5, A-1060, Vienna, Austria

[21] Appl. No.: 831,082

[22] Filed: Feb. 20, 1986

Related U.S. Application Data

[63] Continuation of Ser. No. 379,415, May 18, 1982, abandoned.

[51] Int. Cl.⁴ ..................... A61K 31/44; A61K 31/34
[52] U.S. Cl. .................................. 514/279; 514/282; 514/284; 514/468
[58] Field of Search ..................... 424/155.1; 514/276, 514/288, 126, 468, 284, 282, 279

[56] References Cited

PUBLICATIONS

An Index of Tumor Chemotherapy, 1949, NCI-NIH, pp. 10,11,103,104 and 146.

Primary Examiner—John Rollins
Attorney, Agent, or Firm—Lyon & Lyon

[57] ABSTRACT

A method of diagnosing and for therapeutic treatment of tumors and of infectious diseases by administering effective amounts of cytostatic compositions of alkaloid compounds, their derivatives, salts of the alkaloid compounds, salts of said derivatives or mixtures thereof. The alkaloid component causes stimulation of the cellular defense mechanism, exhibits a great affinity for tumor cells with rapid accumulation in the tumor cells, interferes with cellular activity of tumor cells and cells attacked by virus and other antigens, and destroys malignant tumors and other antigen structures such as viruses, bacteria, fungal organisms. The alkaloid component can be unlabelled or labelled with radioactive isotopes. The compositions may contain materials which are fluorescent under U.V. light or compounds which absorb X-rays. In addition, the compositions can be used as an analgesic in the treatment of polyarthritis and as post-operative anti-inflammation reagent.

9 Claims, 15 Drawing Sheets

CHELILUTIN + THIOPHOSPHORIC ACID TRIAZIRIDIDE

COPTISIN + THIOPHOSPHORIC ACID TRIAZIRIDIDE

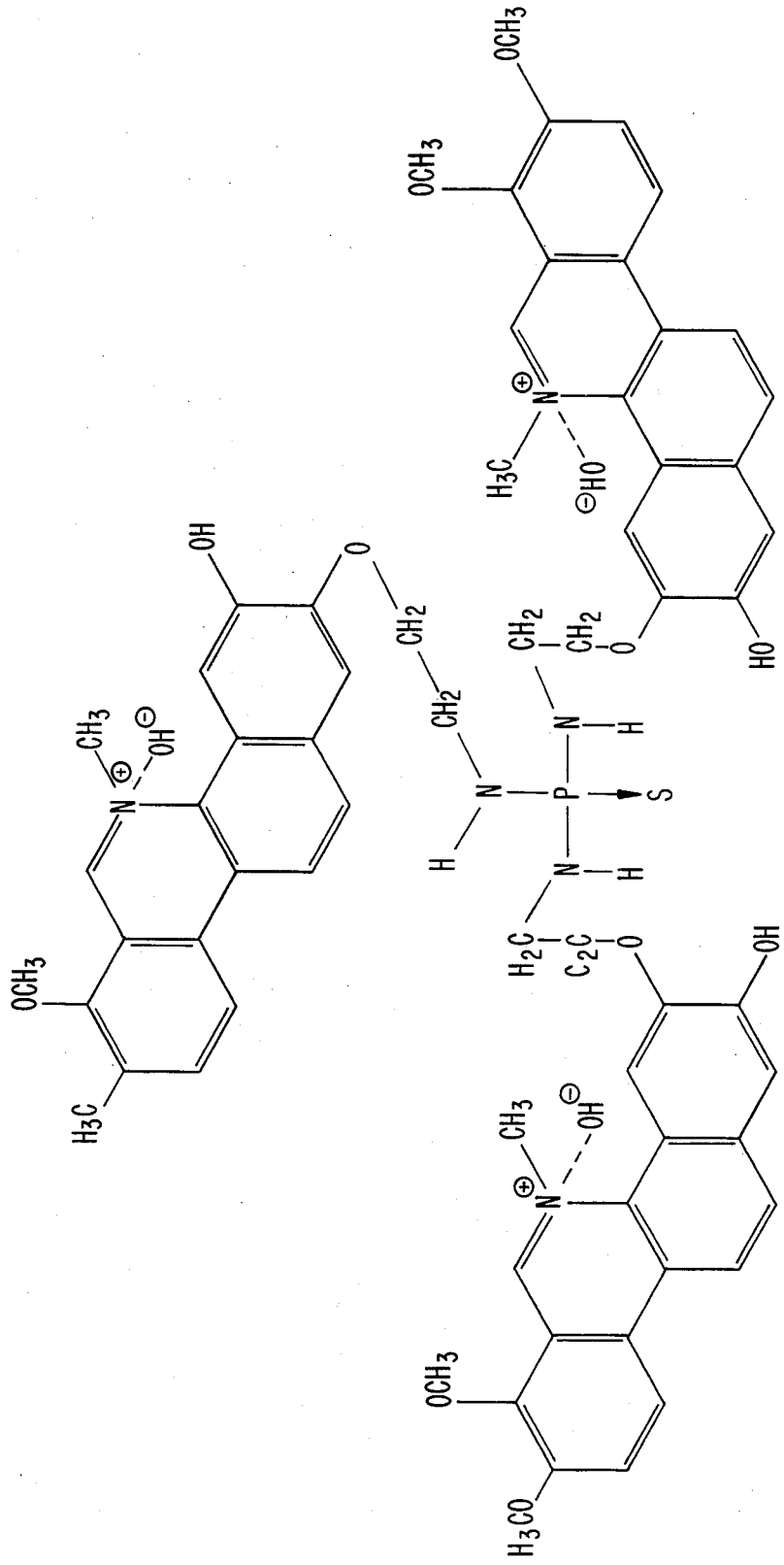
FIG. 2. CHELERYTHRIN + THIOPHOSPHORIC ACID TRIAZIRIDIDE

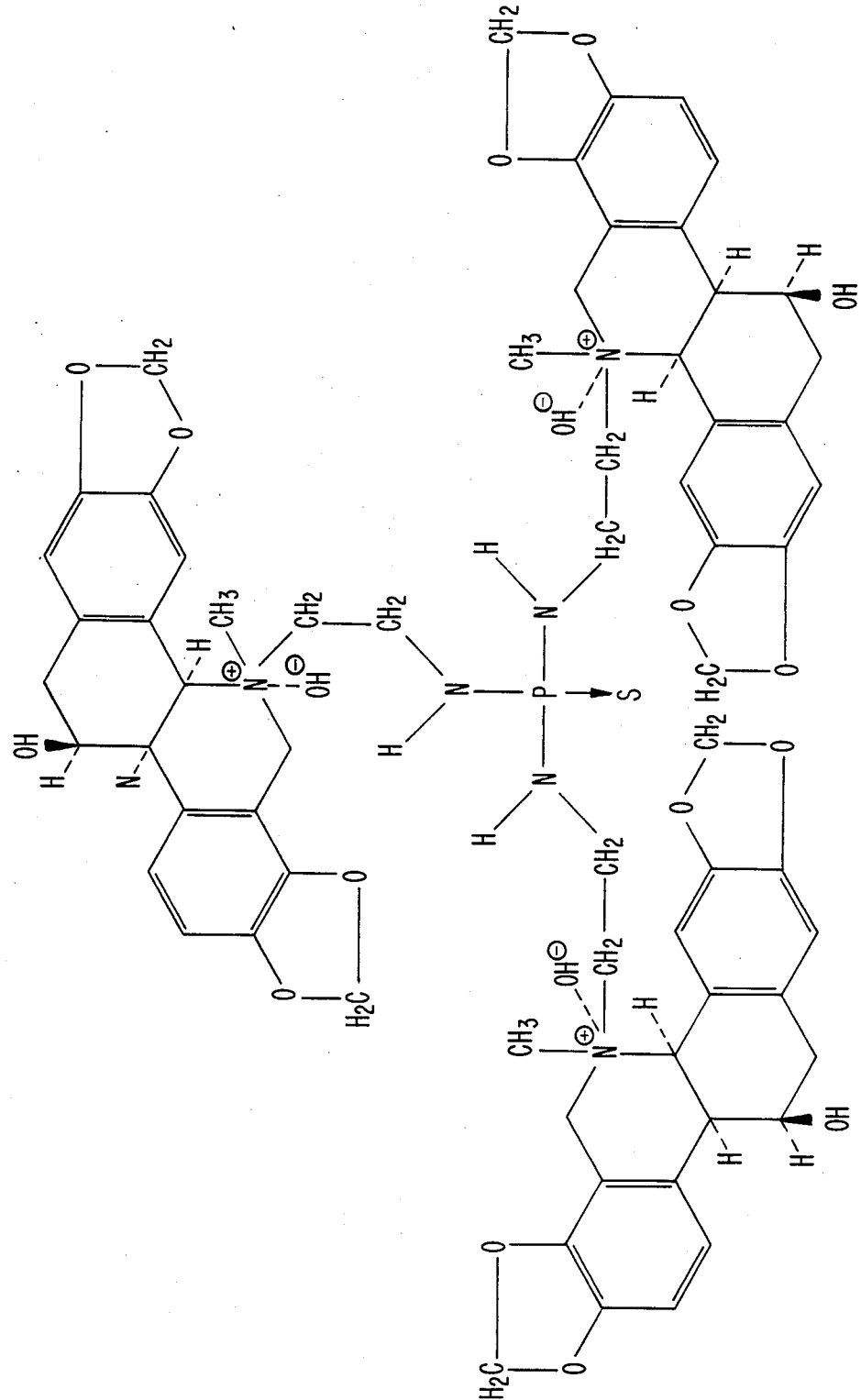
FIG. 4. CHELIDONIN + THIOPHOSPHORIC ACID TRIAZIRIDIDE

PROTOPINE + THIOPHOSPHORIC ACID TRIAZIRIDIDE

METHOD FOR DIAGNOSING AND FOR THE THERAPEUTIC TREATMENT OF TUMORS AND/OR INFECTIOUS DISEASES OF DIFFERENT TYPES WITH ALKALOID-COMPOUNDS

This application is a continuation of application Ser. No. 379,415, filed May 18, 1982, now abandoned.

This application corresponds to my German Patent application No. P 31 28 018.8, filed on July 13, 1981 which is relied upon and incorporated by reference herein.

FIELD OF THE INVENTION

The invention is directed to a method for diagnosing and for therapeutic treatment of tumors and infectious diseases by employing cytostatic derivatives of alkaloids. Those derivatives are also useful as analgesics for the treatment of polyarthritis and as post-operative anti-inflammatory agents.

DESCRIPTION OF THE INVENTION

The invention is directed to a method of diagnosing the presence of tumor cells and for therapeutic treatment of tumors and infectious diseases. The diagnostic and therapeutic reagent is a pharmaceutically acceptable cytostatic derivative of an alkaloid which may also be carcinostatic. The terminology "pharmaceutically acceptable" means at least non-toxic to the host. The alkaloid itself can be cytostatic as well as carcinostatic. The alkaloid derivative is formed by coupling the alkaloid with a compound which may be generically referred as an alkylating reagent which will alkylate the alkaloid, which doesnot interfere with the cytostatic or carcinostatic property of the alkaloid or which is itself cytostatic or carcinostatic. Such alkylating reagents may contain phosphorus and/or nitrogen atoms.

The method of the invention involves administering pharmaceutically effective amounts of said derivative or water soluble pharmaceutically acceptable salts of said derivatives to the host. Administering the reagent may be undertaken by injection or intravenously or subcutaneously. The amounts of the reagent which are administered to the host depend on various factors such as body weight of the host, the stage of disease in the host and the exact nature of the disease and can range from 0.5 mg or less up to 680 mg or more. Generally, the reagents are administered as solutions. A typical aqueous solution to be administered to the host will contain 0.5 mg of the alkaloid derivative in 1 ml of dilute saline solution. The rule in determining dosages for therapeutic purposes is an amount effective to at least retard tumor cell multiplication and, for purposes of diagnosis, to allow accumulation in the tumor tissue of amounts of the reagent sufficient to be detectable. Detection of the accumulated reagent may be undertaken by chemical means, surgery, spectroscopy and/or radiation detection methods well known in the art.

Many alkaloids are described below for use in accordance with the invention to sustain or impart the following common characteristics to the cytostatic derivatives of alkaloids used in accordance with the invention: Stimulation to the cellular defense mechanism; antagonistic to tumor cells and cells attacked by virus and other antigens; having an affinity and capacity for accumulation in tumor tissue.

Alkaloid derivatives of thiophosphoric acid exhibit pharmacological effectiveness as a cytostatic. The word "cytostatic" herein means tending to retard cellular activity and multiplication. Water-soluble salts of those alkaloid derivatives can now be made. Barberine, sanguinarine, salts of alkaloids of the large celandine can be rendered water-soluble as can salts of the bisbenzylisoquinoline-alkaloids, including curine, fangohinolin, tetrandine, pendulin, thalidasine, aporphinebenzylisoquinoline-alkaloids, e.g., thalicarpin, ibogoalkaloids, e.g., 20-hydroxyvoacamidin, indole-indolinealkaloids, e.g., leorosidin, lurosin, vinkaleukoblastin, leurocristin, tropolone alkaloids, e.g., colchicine, isoquinoline-alkaloids, e.g., liriodenin, O-methylatherolin, oxypurpurin, chelidonin, protopine, stylopin, allocryptopine, coptisin, chelerytrin, corysamin, chelidimerin, homochelidonin, methoxychelidonin, chelilutin, chelirubin, narciclasin, talicarpin, pakistanien, pacistanamine, pensylwanin, pensylwanamin, berberine, sanquinarine, caffeine, nitydyne, faraganin, steroidalkaloids, indole-isoquinoline-alkaloids, e.g., 9-methoxyellipticin, ellipticin, indole-alkaloids, e.g., reserpine, quinoline-indolizidin-alkaloids, e.g., campothecin, pyrolin-alkaloids, e.g., tatrofan, pyrolizidin-alkaloids, e.g., heliotrin, acridone-alkaloids, e.g., melicopin, acromycin, normelioepidin, phenanthroindolizidine-alkaloids, e.g., tylophorine, tylocrebin, imidazole-alkaloids, e.g., pilocarpine, quinolizidine-alkaloids, e.g., matrin, oxymatrin, cryptoleurin, chinazolon-alkaloids, e.g., febrifugin, benzuzepin-alkaloids, e.g., cephalotaxin, deoxyharringtonin, homcharringtonin, harringtonin and others.

The thiophosphoric derivatives of alkaloids are also known in the form of free bases and are of interest here. Examples of such known derivatives are thiophosphoric acid-di-(ethyleneimido)-N-berberinol-ethylamide, thiophosphoric acid-tri-(n-sanguinarinol)-ethylamide as well as thiophosphoric acid amido derivatives of the total alkaloids of the condensed isoquinoline systems of the large celandine.

These thiophosphoric derivatives of alkaloids which exhibit cytostatic effectiveness are only sparingly soluble in water. In order to use the derivatives in water, which is preferred to organic solvents for the preparation of injection solutions, the derivatives must be rendered water soluble.

The desired water solubility can be imparted to the active alkaloid derivatives without sacrificing their cytostatic effect and without other undesirable side effects by converting the derivatives to salts of pharmaceutically acceptable acids. The alkaloid, which can also be carcinostatically effective, is coupled with a second carcinostatic agent, preferably from the group consisting of alkylantiene, antimetabolites, antibiotics, and other nitrogen- or phosphorus-containing organic compounds; and the resulting product is converted into a pharmaceutically useable salt. As used herein, the word "carcinostatic" means tending to retard epithelial malignant tumor growth and multiplication. The bases thiophosphoric acid-tri-(N-sanguinarinol)-ethylamine, thiophosphoric acid-di-(ethyleneimido)-N-herberinol-ethylamide as well as N, N', N"-triethylene-thiophosphoramide derivatives of the condensed isoquinoline system-alkaloids are selected from the large celandine (that is, chelidonium majus L.). The aforementioned compounds have proven to be especially suitable as alkaloid components.

The following are especially useful as the second carcinostatic agent for the conversion:

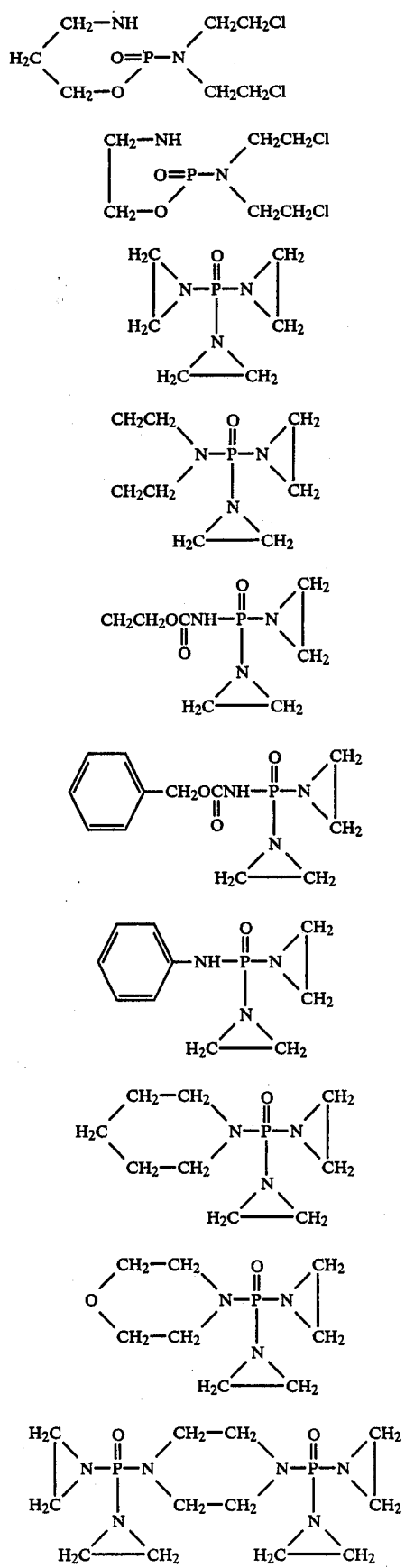
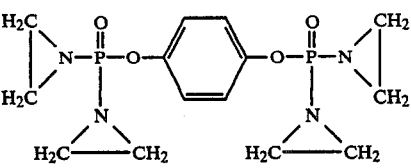
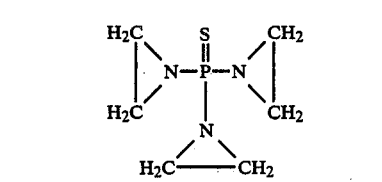
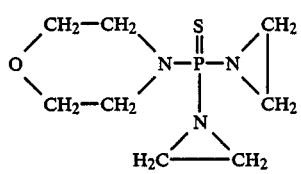
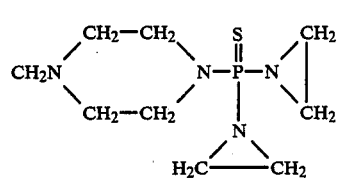
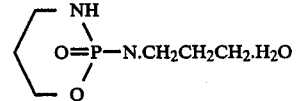
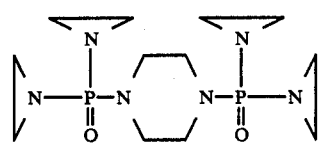
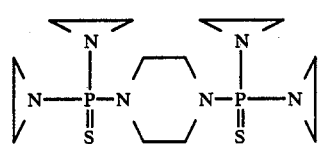
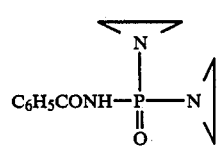
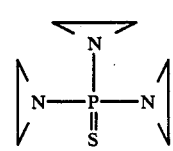

-continued

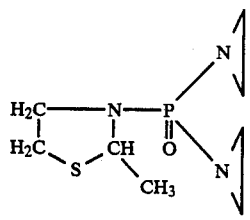

Nitrogen mustard gas, cyclophosphamide, triamcichon, chlorambucil, busulfan,

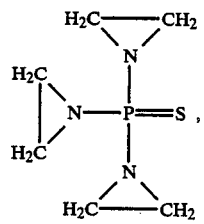

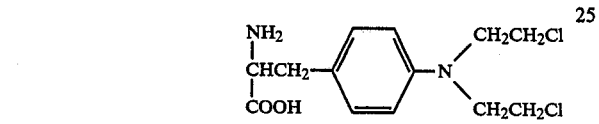

nitomin, mannitol-nitrogen mustard gas, amethopterin, 6-mercaptopurin, 5-fluorouracil, cytosine-arabinosid.

Podophyllin, actinomycin C, actinomycin D, mithramycin, mitomycin C, adriamycin, bleomycin, asparaginase, ibenzmethycin.

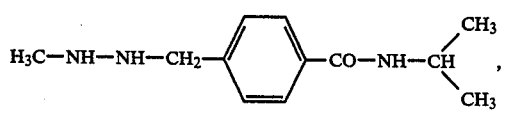

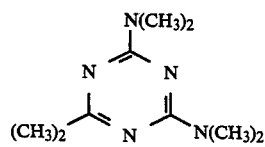

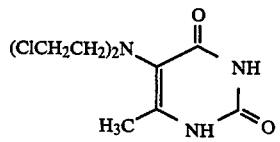

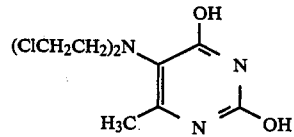

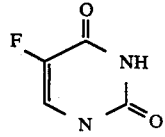

-continued

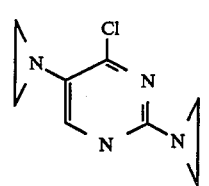

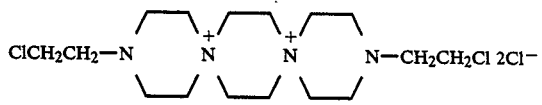

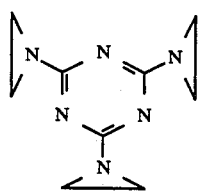

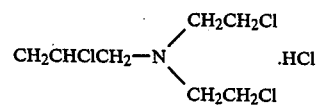

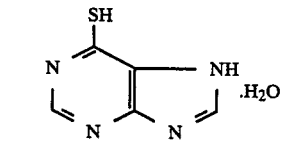

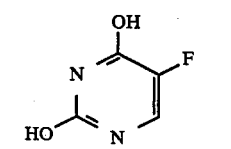 (XXI)

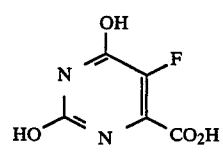 (XXIII)

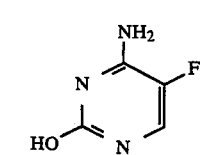 (XXIV)

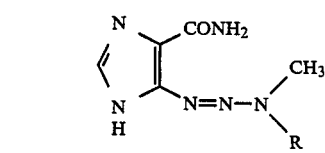

where R=H or CH$_3$.

Phosphorus derivatives of alkaloids corresponding to formula (I) below are of particular interest:

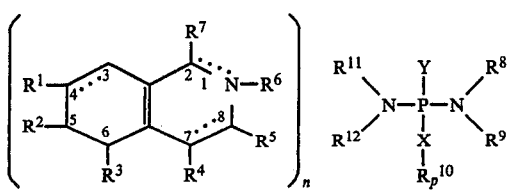 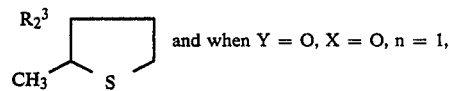

where each of $R^1$, $R^2$ and $R^3$ is hydrogen or methoxy, independently of each other or where $R^1$ and $R^2$ or $R^2$ and $R^3$ together can also represent a methylene dioxy group:

Where $R^4$ and $R^5$ can be H or together with the C-atoms to which they are bonded, form a completely or partially hydrated phenyl- or naphthyl group, which phenyl- or naphthyl group can be unsubstituted or substituted by methoxy, hydroxy, or dioxymethyl, when $R^7$ is H or =O (oxygen atom) or it is an equal ring system bound over a $CH_2$—$CO$—$CH_2$-chain, $R^6$ is CH and double bonds can be present in position 1, 2 and/or 7, 8; or $R^6$ and $R^7$, together with the C and N-atom, to which they are bonded, form a partially hydrated benzo-or naphtho ring system, which can be unsubstituted or substituted by methoxy, oxo, methyl or dioxymethyl groups, where the C—N-bond can be missing in position 1, 2 and $R^4$ and $R^5$ mean H;

$R^8+R^9$ and $R^{11}+R^{12}$ mean —$CH_2$—$CH_2$ and if Y=S, X=N and p=2, then $R^8+R^9$ and $R^{11}+R^{12}$ is $R_2^3$ —$CH_2$—$cH_2$—, —$CH_2$—$CH_2$—$O$—$CH_2$—$CH_2$— or

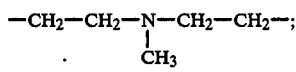

when Y=S, X=N, n=2 represents $R_2^3$ —$CH_2$—$CH_2$—,

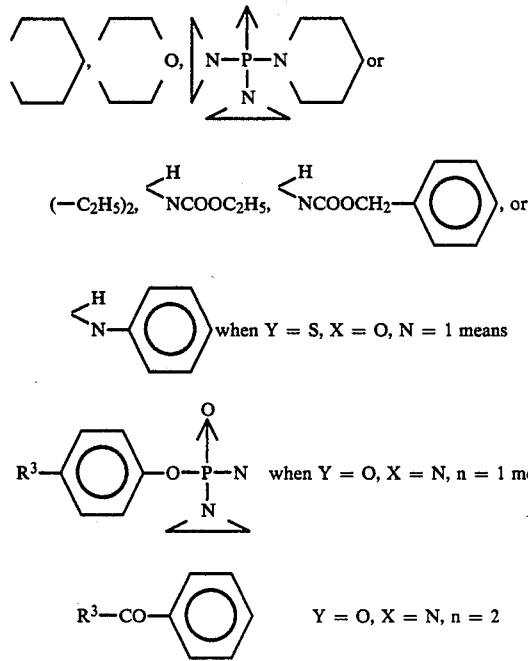

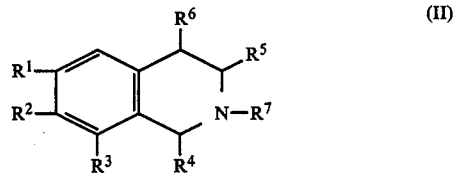

$R^8$ and $R^9$ each mean —$CH_2$—$CH_2$—Cl, $R^{11}$ H and $R^{10}+R^{12}$ mean —$CH_2$—$CH_2$— or —$CH_2$—$CH_2$—$CH_2$—, when Y=S, X=N, p=1, $R^3$ —$CH_2$—$CH_2$—

The salt formation of the phosphorus derivatives of the alkaloids can be carried out with practically any pharmaceutically acceptable acid, which in itself is sufficiently water-soluble, and thus provides sufficiently water-soluble salts. For economic reasons, hydrochloric acid is preferably used.

The resulting alkaloid thiophosphoric acid amide salts do not differ in their cytostatic or in their pharmacological effectiveness from the corresponding bases. However, dosage preparation of the salts is easier and more exact due to their substantially increased water solubility. Furthermore, no disturbing side effects which can be ascribed to the organic solvents necessary for the corresponding water-insoluble bases can occur.

Salts, especially hydrochloride of berberine or sanguinarine, as well as finally the salts of the alkaloids of the large celandine and other alkaloids come into question as alkaloid salts of formula (II) (compare here also the structure formulas of FIGS. 1 to 17).

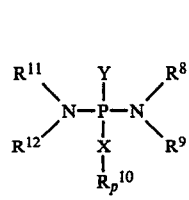

The cytostatic derivative of the alkaloid can be prepared in one of two ways. The conversion of the alkaloid salts with the cytostatic medium is advantageously carried out in a solvent or solvent mixture at elevated temperature generally at the reflux temperature. Alternatively, the alkaloid base can first be reacted with the thiophosphoric acid amide, after which the reaction product can be converted into the salt, for example by saturating the solvent solution of the alkaloid derivative with HCl (gas and allowing the HCl saturated solution to stand. The reaction of the compound of the alkaloid with the cytostatic and with the acid is advantageously carried out in an organic solvent, where, after salt formation, the actual salt precipitates out or it can be extracted by shaking out with water or hydrous acid into the aqueous solution. Organic solvents used will vary with the alkaloid composition. By way of example, it is noted that benzene, dioxane (anhydrous), and a mixture of ether (anhydrous) and dichloroethane have been used as solvents for thiophosphoric acid-tri-(N-sanguinarinol)-ethyl amide, berberine hydrochloride and a mixture of the alkaloid extract of the great celandine and thiophosphoric acid-triethylene amide.

The alkaloid component of compositions administered in accordance with the invention may contain one or more cytostatic alkaloid derivatives, which will be explained below.

The composition of a preparation, for example, one which consists of alkaloids of Chelidonium majus L., is based on the reaction of the alkaloids with an alkylating substance, such as thiophosphoric acid triaziridide (Thio-TEPA). This substance Thio-TEPA, has three reactive groups, which either bind with the alkaloid molecules or can be substituted by OH or $NH_2$ groups. A whole series of different reaction products can originate in this manner, if this substance binds with an individual, pure alkaloid. In order to study simpler reactions, individual alkaloids were mixed with Thio-TEPA, cyclophosphamide and other organic compounds in test series. In the case of chelidonin, at least 12 reaction products can be proven by thin-layer chromatography. In order to obtain an exact analysis of these reaction products some were crystallized and isolated by chromatography and subjected to elemental analysis as will be described in the Description of the Drawings.

DESCRIPTION OF THE DRAWINGS

The following figures of the drawings designate the possible molecular structure based on elemental analysis of the products produced in the reaction on between individual alkaloids and Thio-TEPA, cyclophosphamide and the like. In the description below, the respective alkaloid and phosphorus compounds are described after the numerical designation for the corresponding figure, followed by the actual and calculated elemental analysis for the product.

FIG. 2 Chelerythrin+Thiophosphoric acid triaziridide $C_{66}H_{69}N_6O_{15}PS$.
Calculated: C=63.45%; H=5.56S%; N=6.73%; P=2.47%. Found: C=62.69%; H=5.37%; N=5.37%; P=2.35%.

FIG. 4. Chelidonin+Thiophosphoric acid trizairidide $C_{66}H_{75}N_6O_{18}PS$.
Calculated: C=60.82%; H=5.79%; N=6.44%; P=2.37%; S=2.45%. Found: C=61.41%; H=5.76%; N=5.94%; P=2.40%; S=2.39%.

Figure 1:
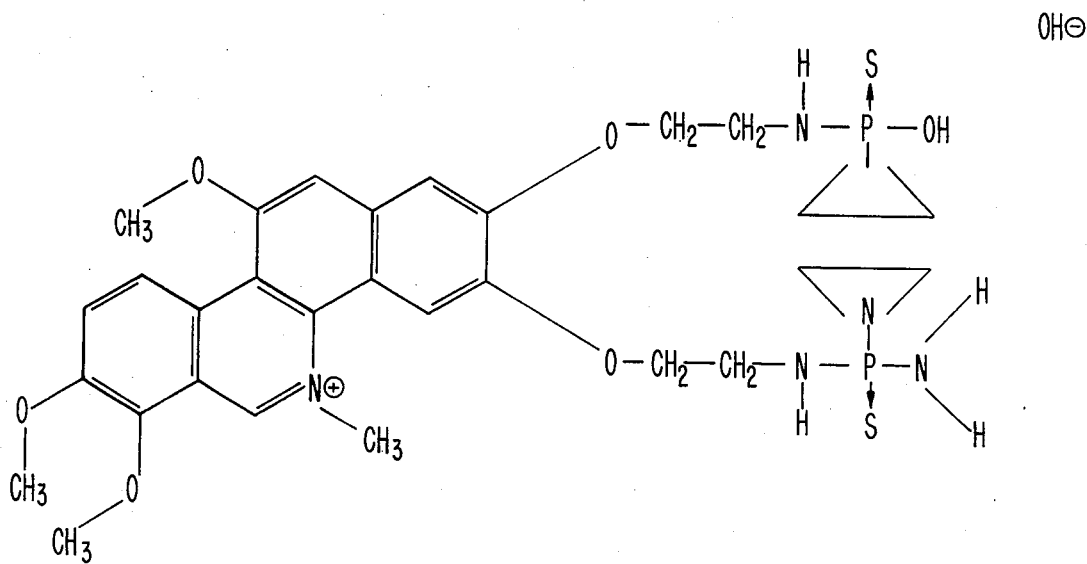
FIG. 1. Chelilutin+Thiophosphoric acid triaziridide (1-Chelilutin, 2-thiophosphoric acid triaziridide, 3-chelilutin+thiophosphoric acid triaziridide).
Calculated: C=49.44%; H=6.36% N=11.53%; P=8.49%. Found: C=49.41%; H=6.34%; N=10.65%; P=8.67%.
Figure 3:
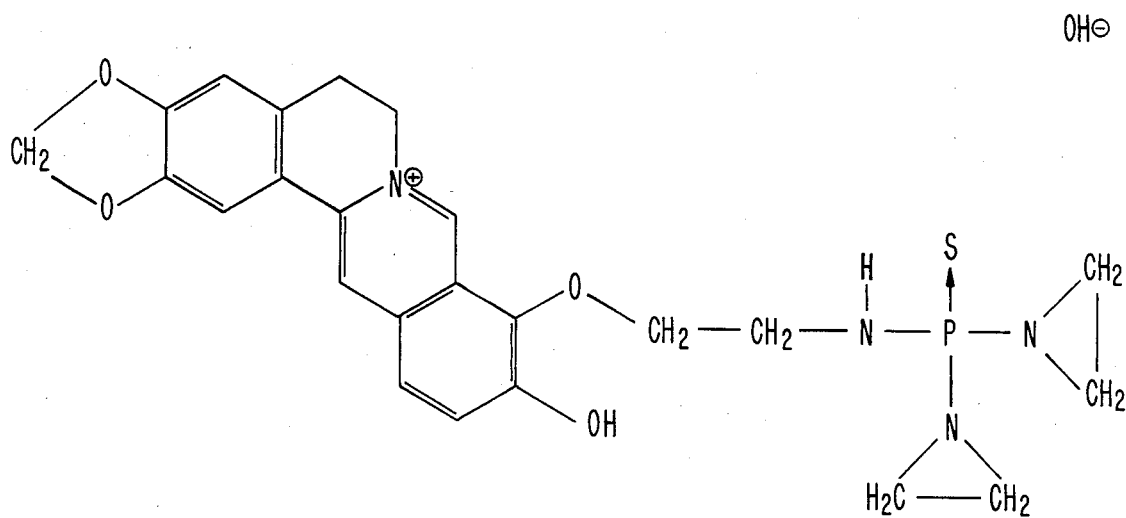
FIG. 3. Coptisin+Thiophosphoric acid triaziridide $C_{24}H_{27}N_4U_5PS$.
Calculated: C=56.02%; H=5.28%; N=10.88%; P=6.01%; S=6.23%. Found: C=55.94%; H=5.12%; N=11.10%; P=5.89%; S=6.10%.
Figure 5:
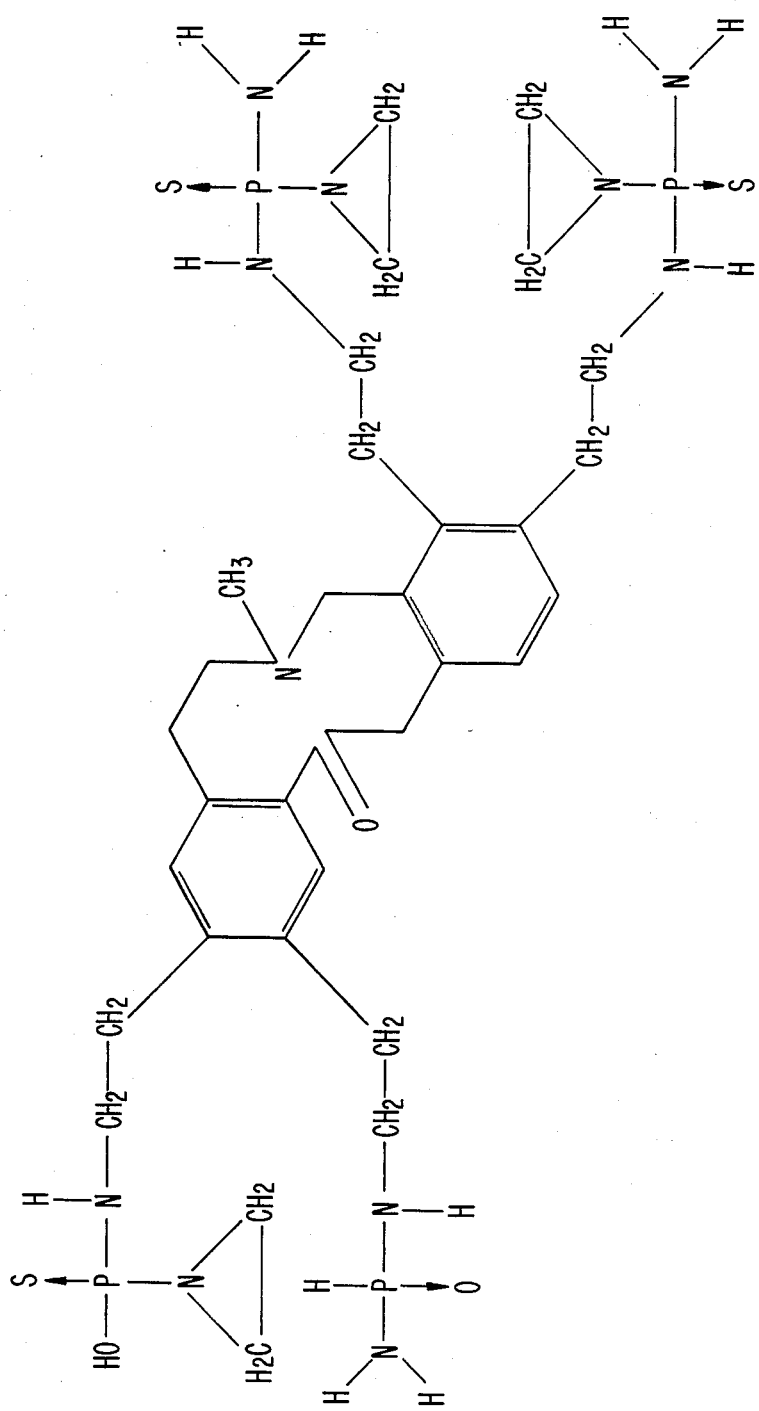
FIG. 5. Protopine-thiophosphoric acid triaziridide $C_{32}H_{55}N_{11}P_4S_3$.
Calculated: C=44.59%; H=6.43%; N=17.87%; P=14.37%; S=11.16%. Found: C=44.58%; H=6.14%; N=17.76%; C=44.72%; H=6.30%; N=17.77%; P=14.04%; S=12.71%.
Figure 6:
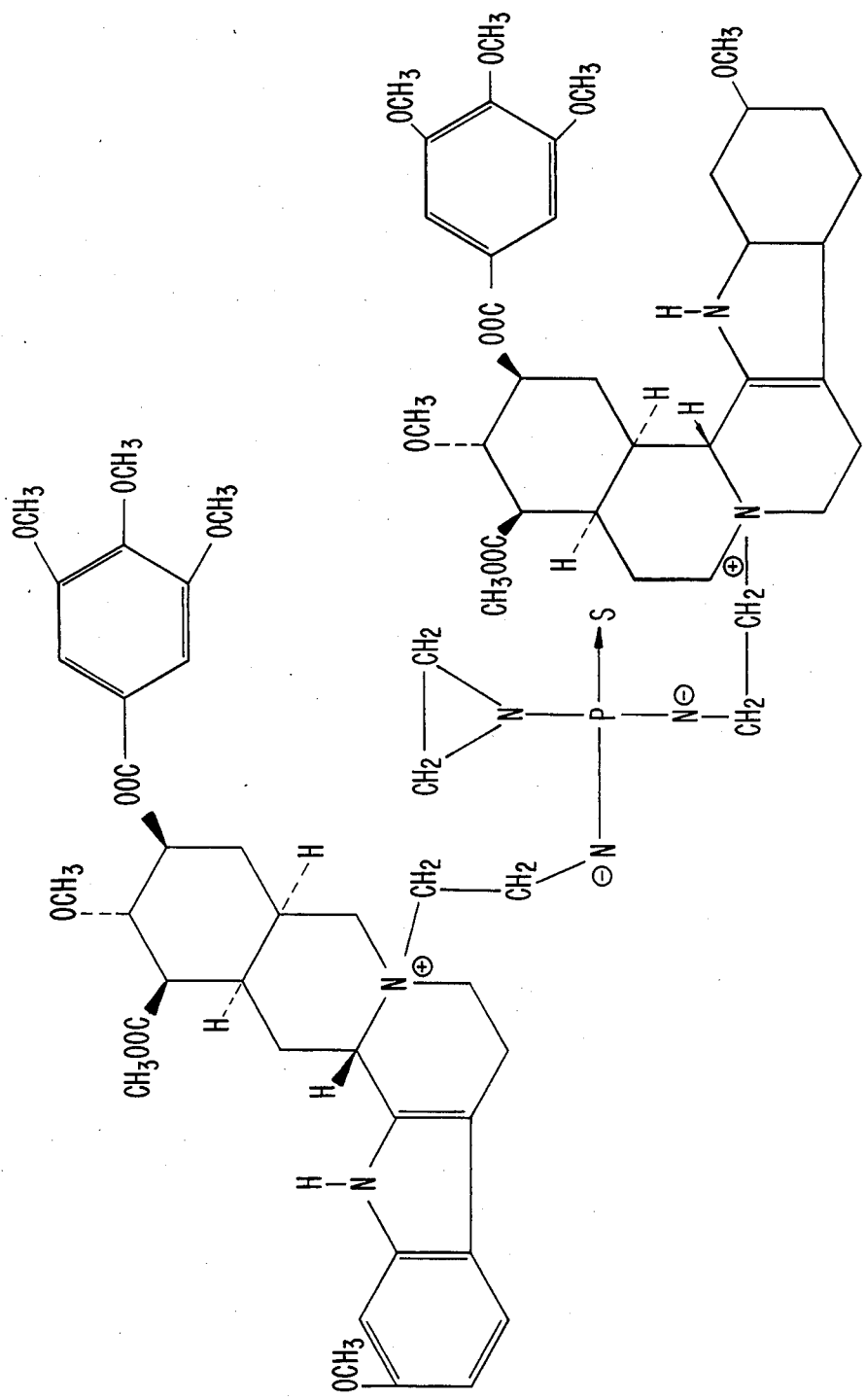
FIG. 6. Reserpine=thiophosphoric triaziridide $C_{72}H_{92}N_7PSO_{18}.2H_2O$, mp 120°–125°.
Theor.: C=59.94%; H=6.70%; N=6.79%; P=2.14%; S=2.22%. Found: C=59.89%; H=6.62%; N=6.82%; P=2.21%; S=2.26%.
Figure 7:
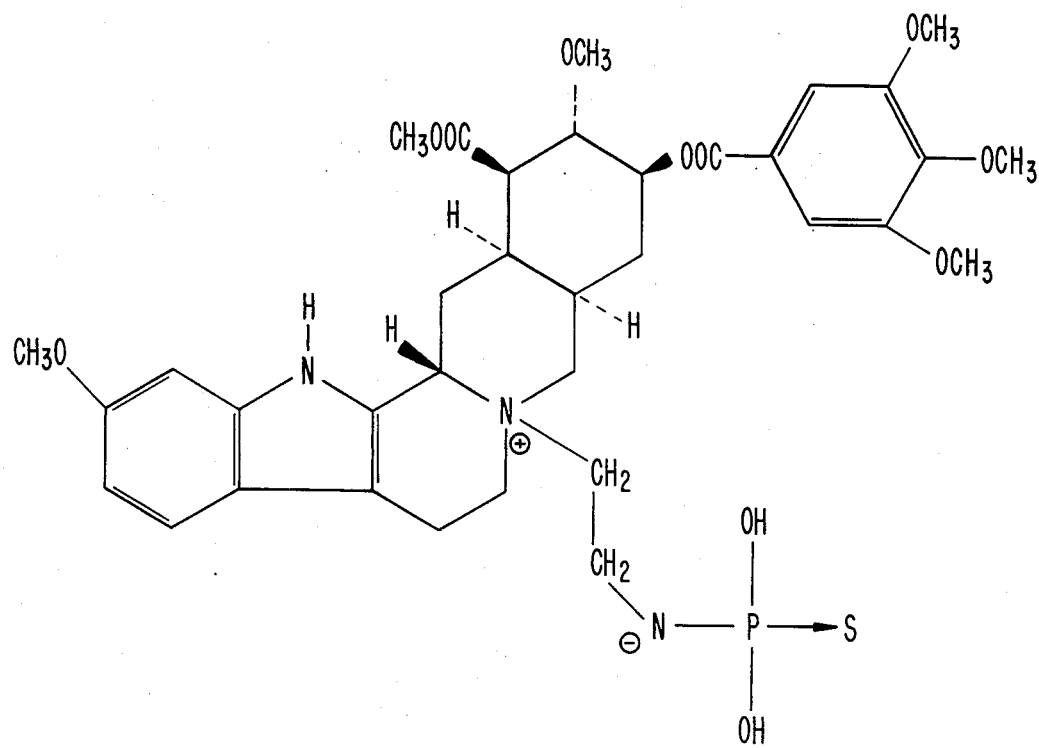
FIG. 7. Reserpine+thiophosphoric triaziridide $C_{35}H_{46}N_3O_{11}PS$.
Theor.: C=56.21%; H=6.20%; N=5.61%; P=4.14%; S=4.28%. Found: C=56.3%; H=6.22%; N=4.11%.
Figure 9:
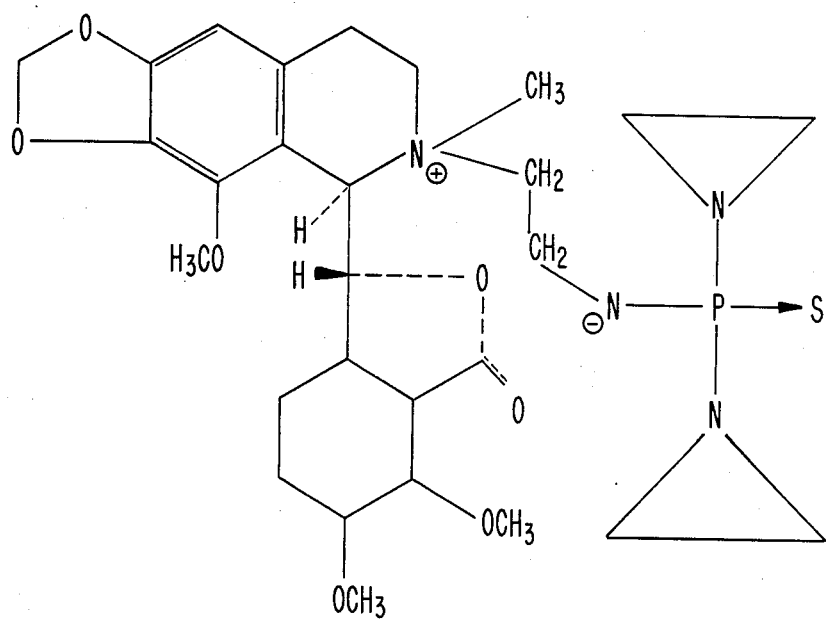
FIG. 9. Narcotine+thiophosphoric triaziridide $C_{28}H_{35}N_4PSO_7$, mp 225°–226°.
Theor.: C=55.80%; H=5.85%; N=9.29%; P=5.13%; S=5.29%. Found: C=55.34%; H=5.69%; N=9.52%; P=4.80%; S=5.29%.
Figure 8:
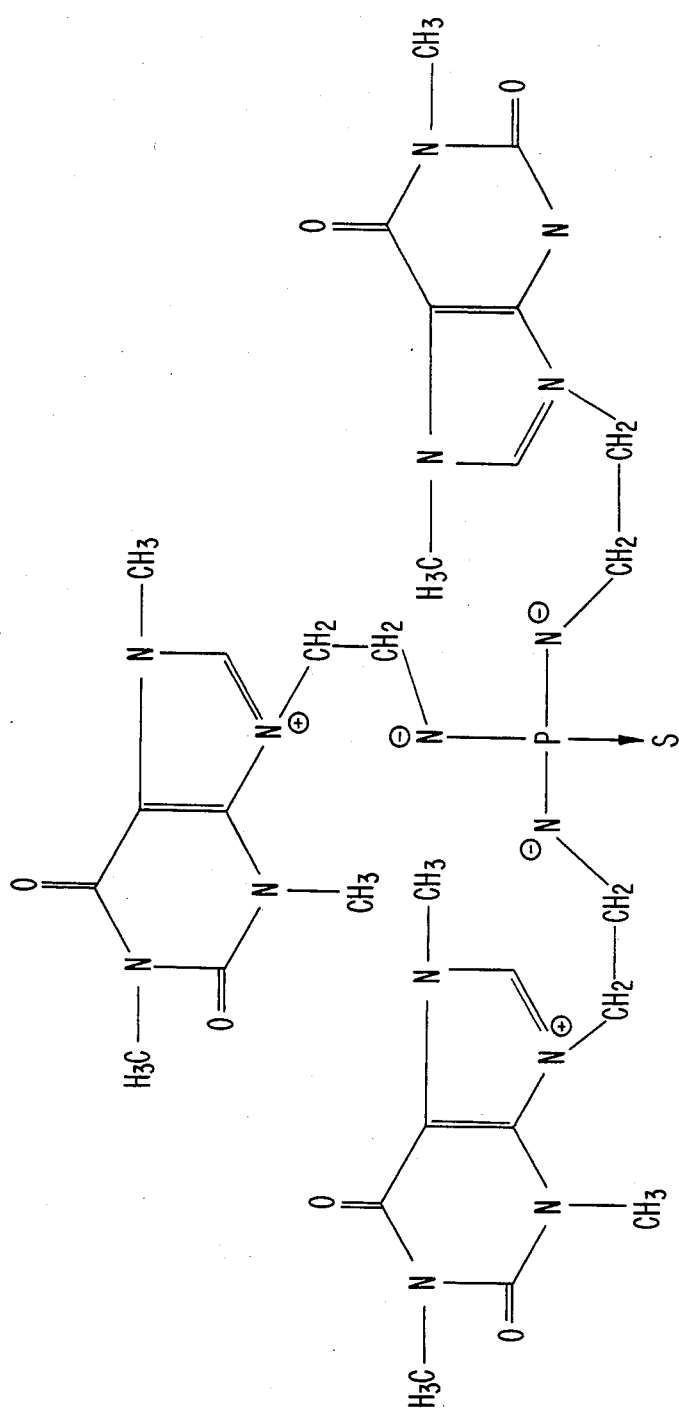
FIG. 8. Caffeine+thiophosphoric triaziridide $C_{30}H_{42}N_{15}PSO_6$, mp 110°–112°; 215°–216°.
Theor.: C=46.68%; H=5.48%; N=27.22%; P=4.01%; S=4.15%. Found: C=47.37%; H=5.44%; N=27.25%; P=4.02%; S=4.15%.
Figure 10:
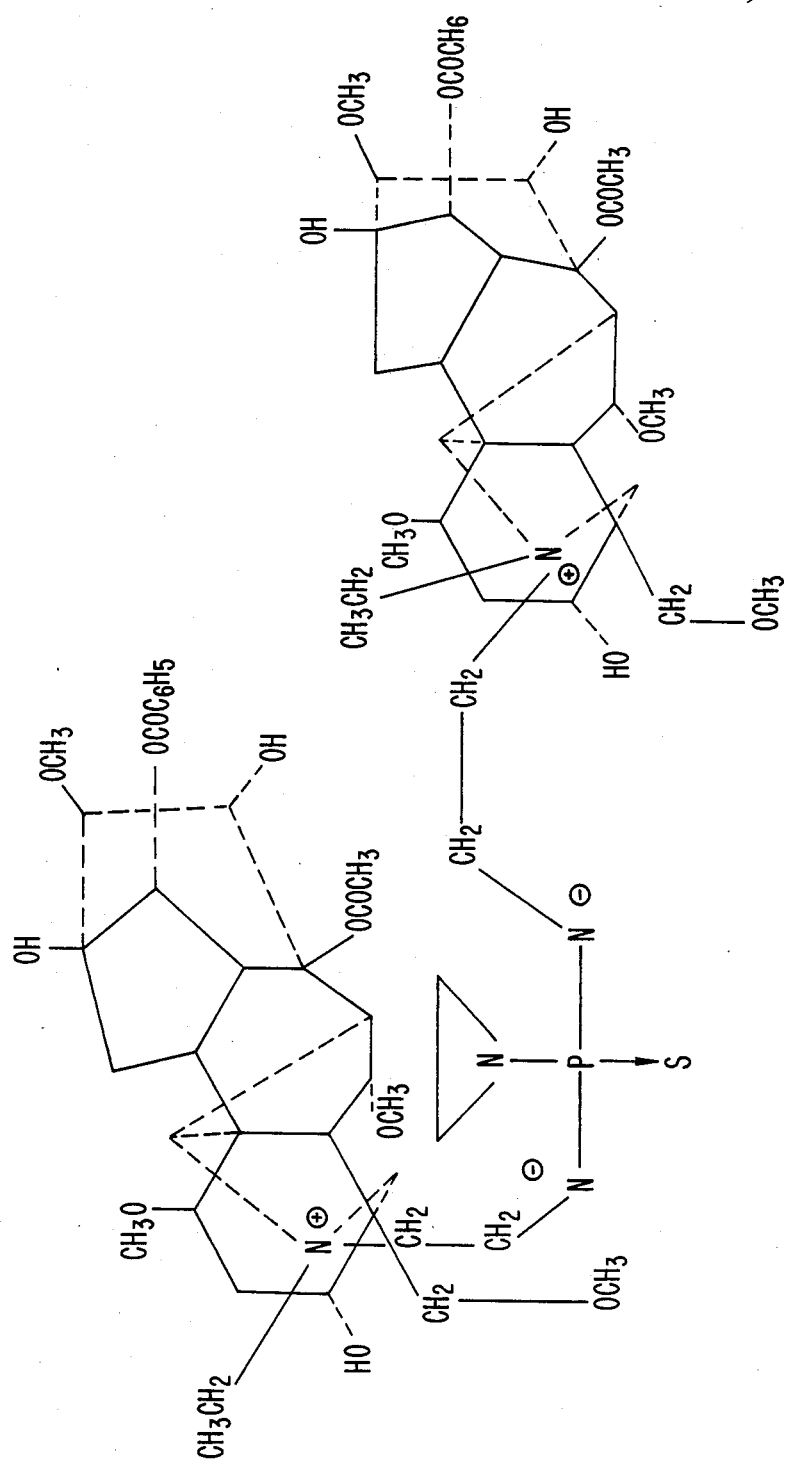
FIG. 10. Aconitine+thiophosphoric triaziridide $C_{74}H_{106}N_5O_{22}PS$, mp 197°–200°.
Theor.: C=60.02%; H=7.21%; N=4.72%; P=1.09%; S=2.16%. Found: C=60.02%; H=7.21%; N=4.38%; P=2.09%; S=2.16%.
Figure 11:
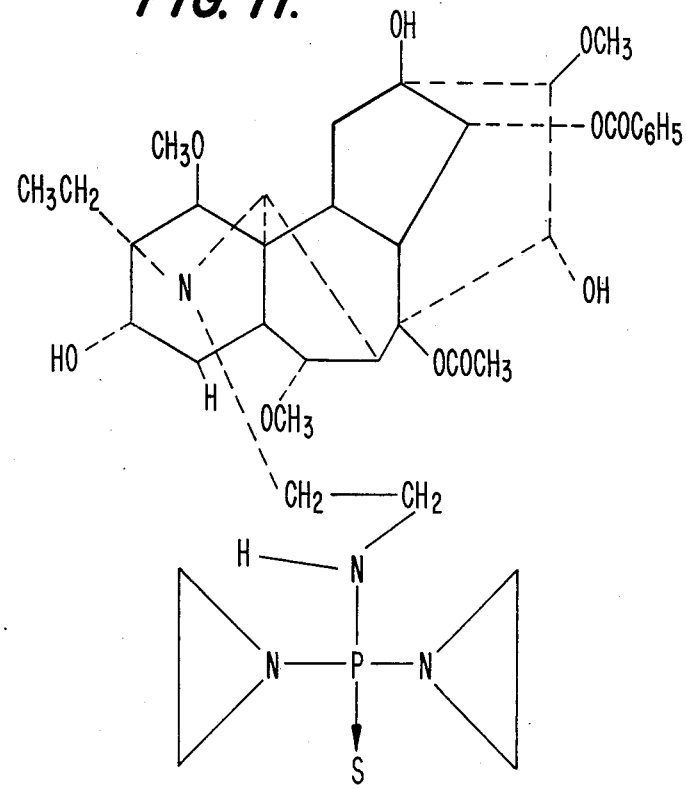
FIG. 11. Aconitine+thiophosphoric triaziridide $C_{39}H_{59}N_4O_{11}PS$, mp 210°–211°.
Theor.: C=56.92%; H=7.22%; N=6.80%; P=3.76%; S=3.86%. Found: C=56.91%; H=7.12%; N=6.89%; P=3.60%; S=3.73%.
Figure 12:
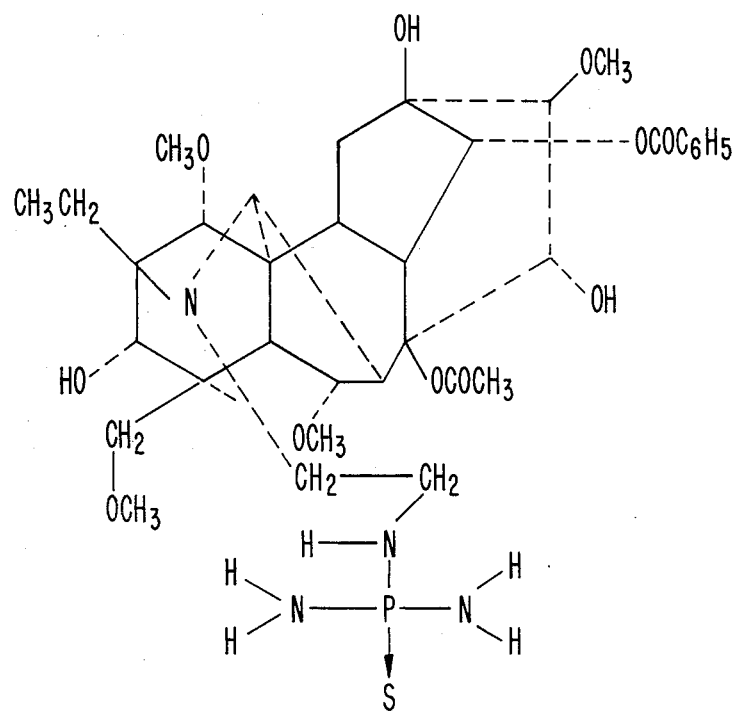
FIG. 12. Aconitine+thiophosphoric triaziridide $C_{35}H_{55}N_4PSO_{11}$, mp 190°–192°.
Theor.: C=54.83%; H=7.19%; N=7.26%. Found: C=54.83%; H=6.98%; N=8.74%.
Figure 13:
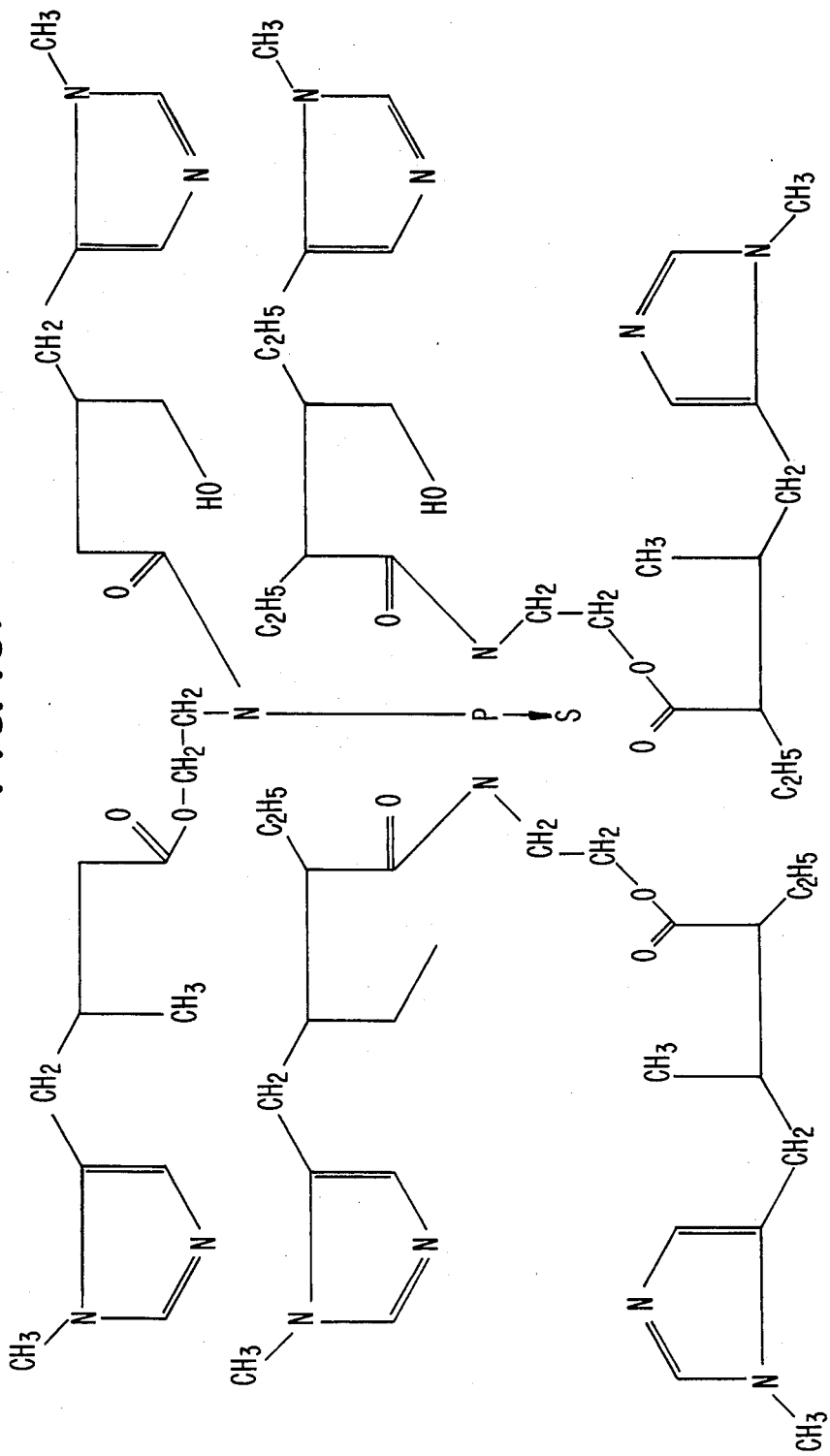
FIG. 13. Pilocarpine+thiophosphoric triaziridide $C_{26}H_{31}N_3O_7$.
Figure 14:
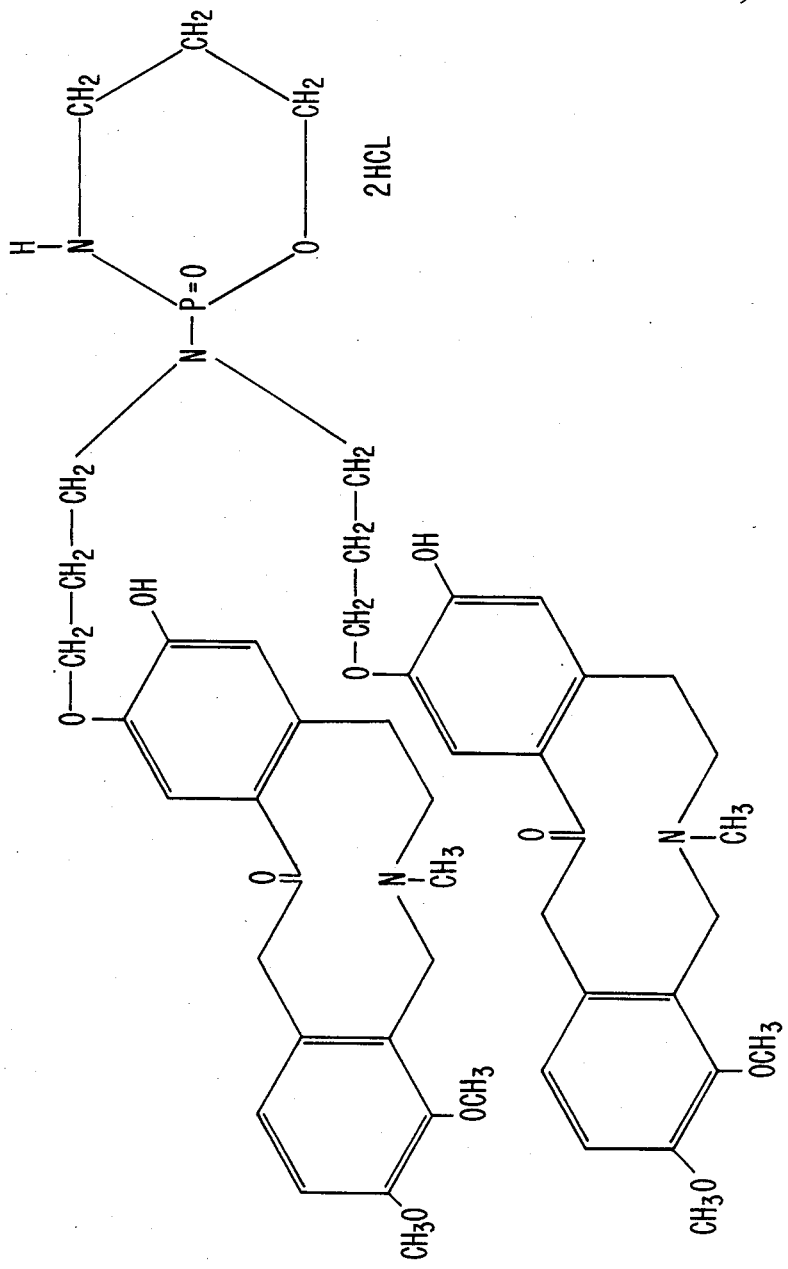
FIG. 14. Allocryptopine+cyclophosphamide (N,N-bis-($\beta$-chloroethyl)-N,O-propylenephosphoric acid ester diamide) $C_{49}H_{65}N_4O_{12}Cl_2P$, mp 159°–160°.
Theor.: C=8.25%; H=6.29%; N=5.58%; P=3.08%; Cl=7.06%. Found: C=58.25%; H=6.25%; N=5.40%; P=2.53%; Cl=7.41%; C=54.84%; H=6.16%; N=5.62%; P=2.51%; Cl=7.26%.
Figure 15:
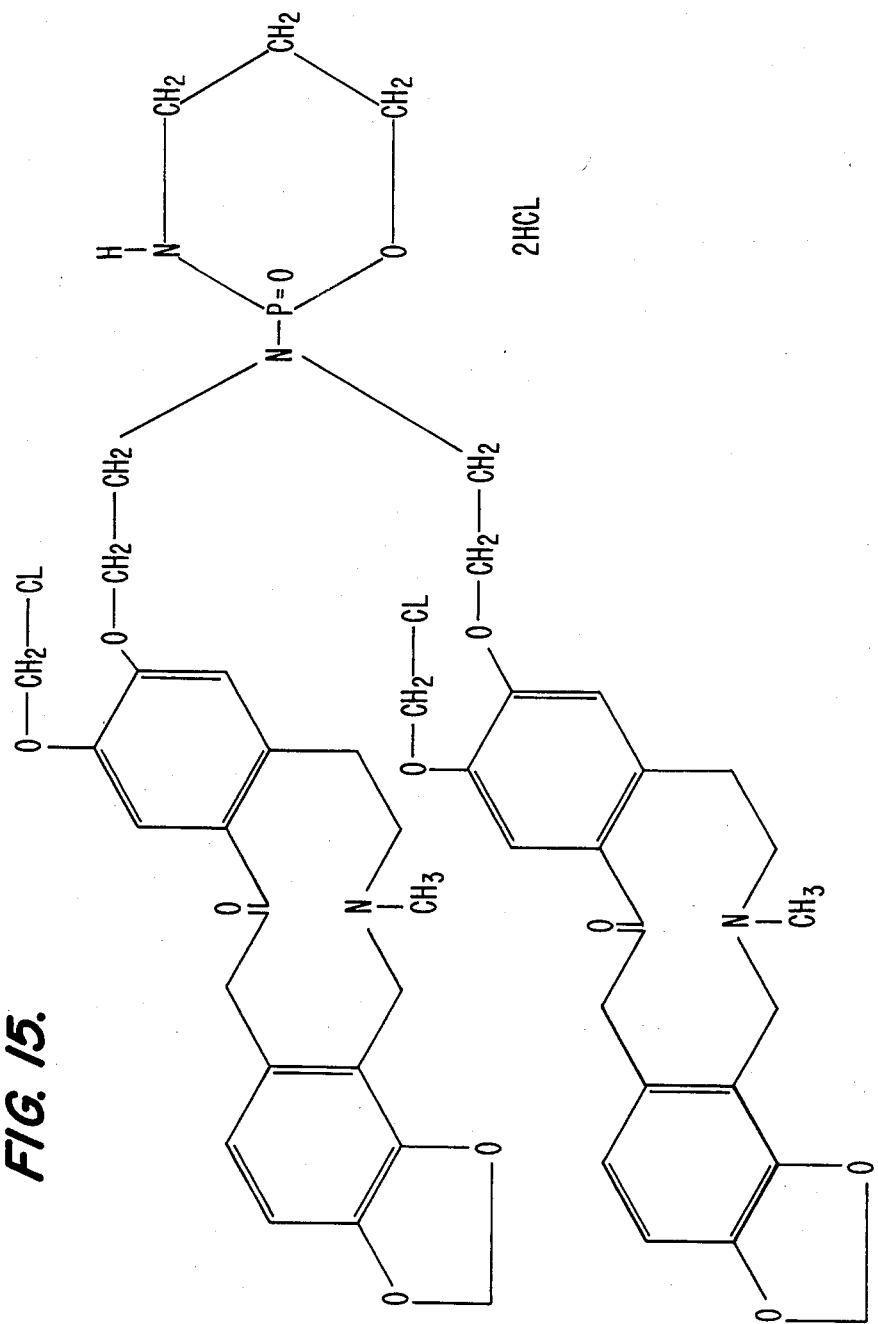
FIG. 15. Protopine+cyclophosphamide (N,N-bis-($\beta$-chlorethyl)-N,O-propylene phosphoric acid ester diamide) $C_{47}H_{55}N_4O_{12}PCl_4$, mp 239°–242°.
Theor.: C=54.24%; H=5.32%; N=5.38%; P=2.97%; Cl=13.62%. Found: C=54.04%; H=5.25%; N=4.85%; P=2.72%; Cl=10.13%; C=54.48%; H=5.22%; N=4.69%; Cl=9.91%.
Figure 15A:
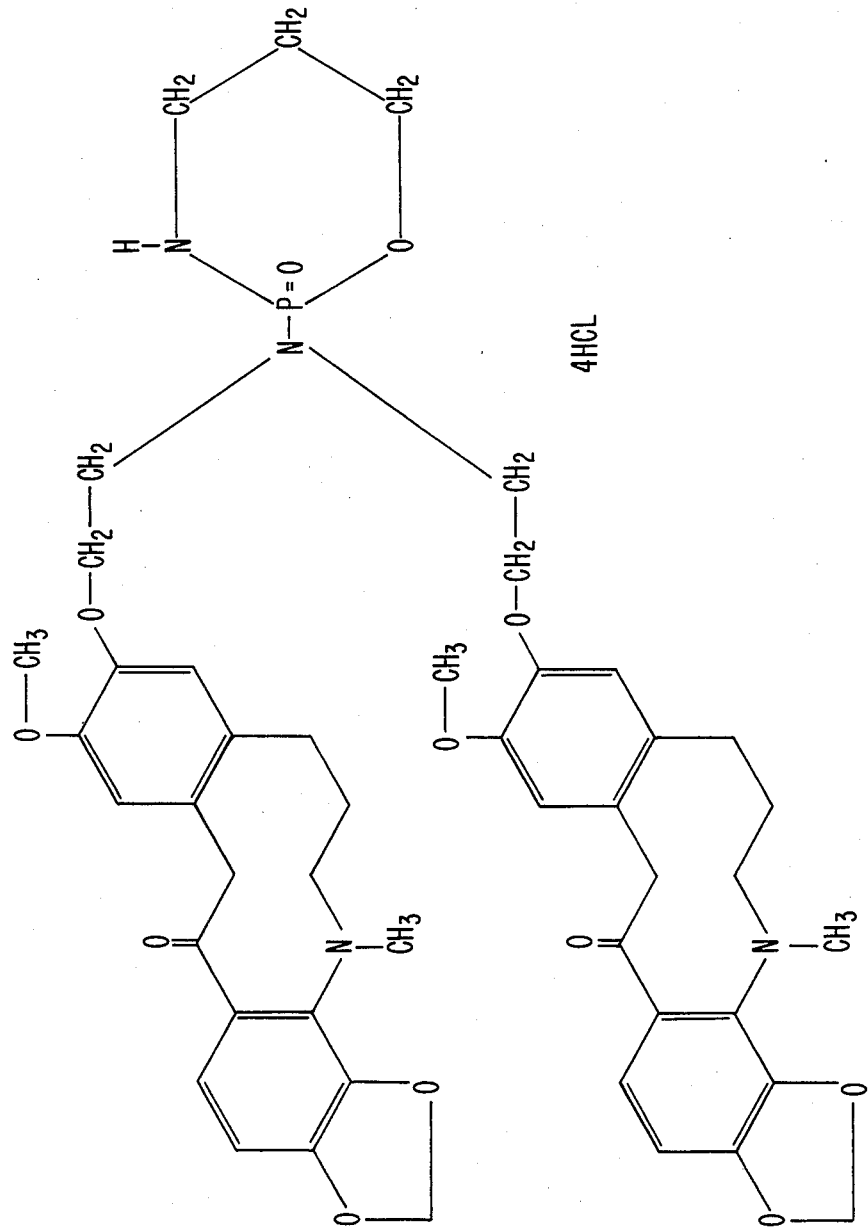
FIG. 15a. Protopine+cyclophosphamide (N,N-Bis'($\beta$-chlorethyl)-N',O-propylene phosphoric acid ester diamide) $C_{47}H_{59}N_4O_{12}PCl_4$, mp 239°–242°.
Theor.: C=54.03%; H=5.69%; N=5.36%; P=2.96; Cl=13.57%. Found: C=54.04%; H=5.25%; N=4.85%; P=2.27; Cl=10.13%; C=54.48%; H=5.22%; N=4.69%; Cl=9.91%.
Figure 15B:
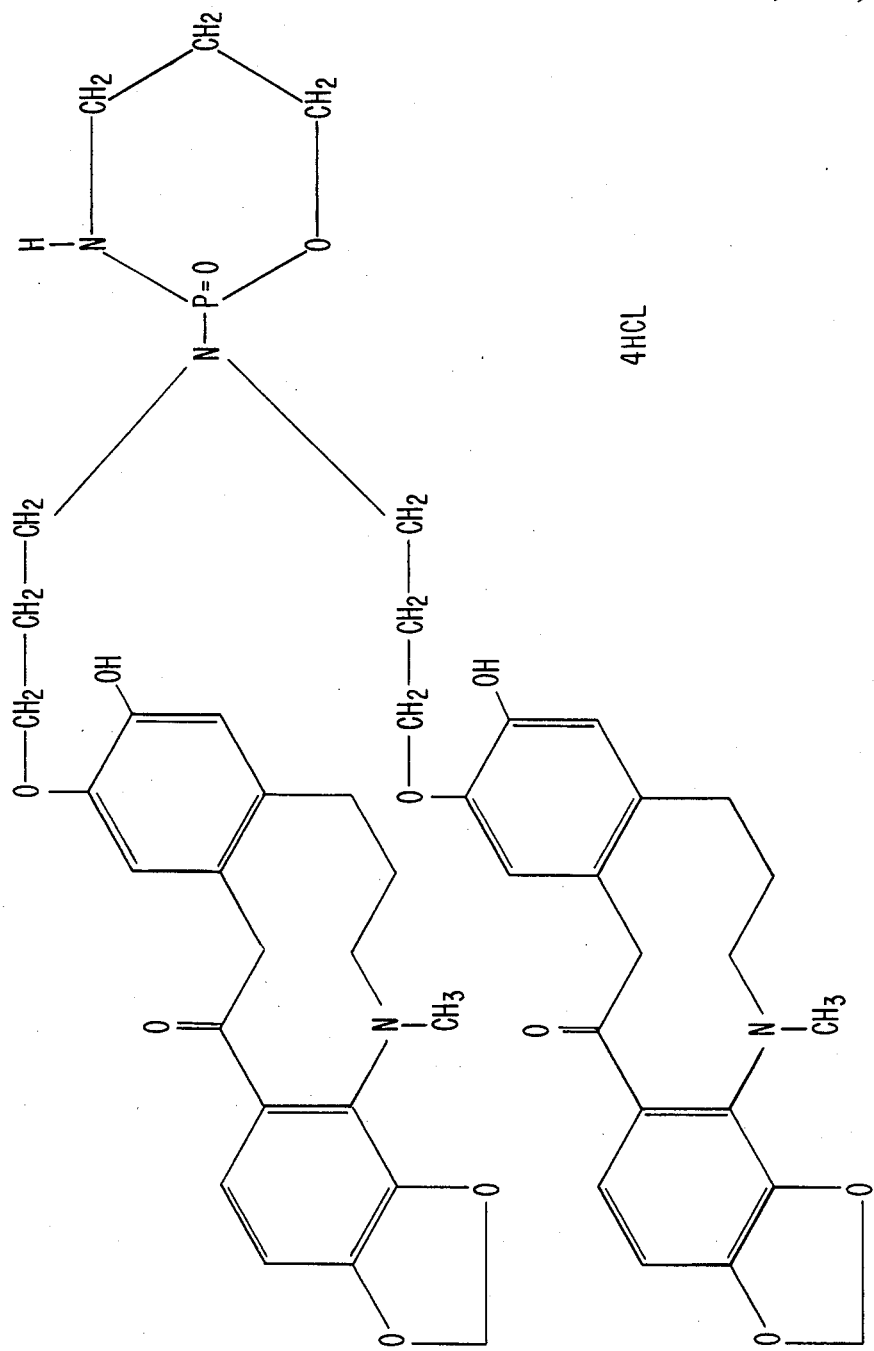
FIG. 15b. Protopine+cyclophosphamide (N,N-bis-($\beta$-chlorethyl)-N',O-propylenephosphoric acid ester diamide) $C_{47}H_{59}N_4O_{12}PCl_4$, mp 239°–242°.
Theor.: C=54.03%; H=5.69%; N=5.36%; P=2.96%; Cl=13.57%. Found: C=54.04%; H=5.25%; N=4.85%; P=2.27%; Cl=10.13%; C=54.48%; H=5.22%; N=4.69%; Cl=9.91%.
Figure 16:
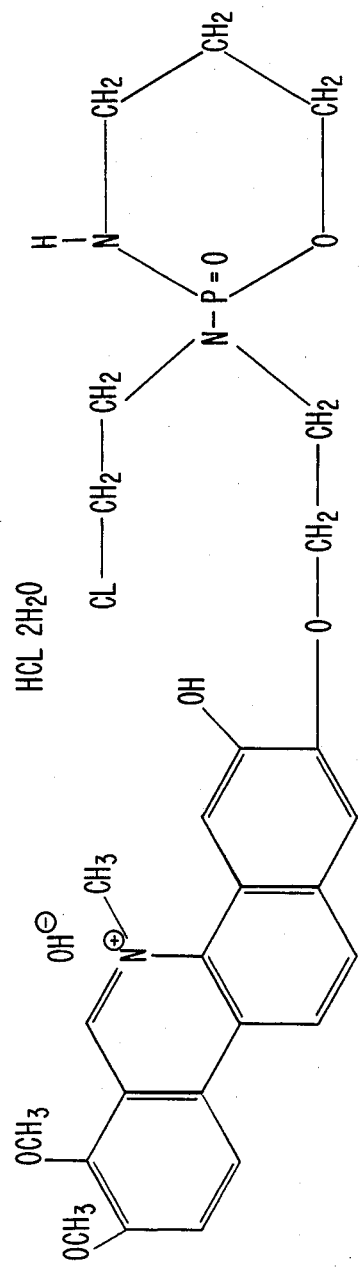
FIG. 16. Chelerythrine+cyclophosphamide (N,N-bis-($\beta$-chlorethyl)-N',O-propylene phosphoric acid diamide) $C_{27}H_{37}N_3O_9PCl_2$, mp 188°–192°.
Theor.: C=49.93%; H=5.74%; N=6.64%; P=4.76%; Cl=10.91%. Found: C=49.85%; H=5.31%; N=6.06%; P=4.95%; Cl=13.23%; C=49.84%; H=5.24%; N=5.96%; Cl=14.24%.
Figure 17:
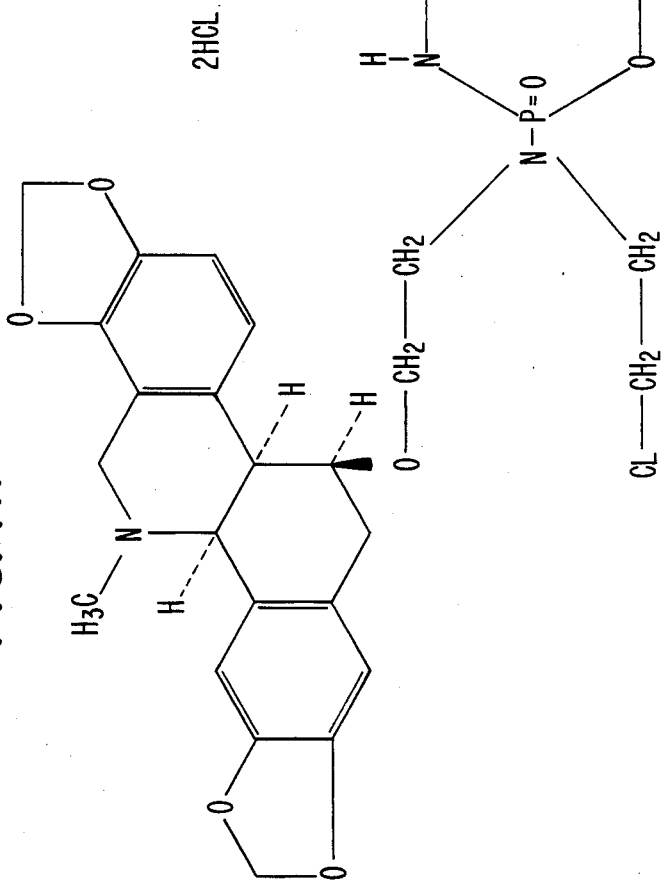
FIG. 17. Chelidonine+cyclophosphamide (N,N-Bis'($\beta$-chloroethyl)-N'O-propylene phosphoric acid ester diamide $C_{27}H_{35}N_3O_7PCl_3$, mp 273°–276°.
Theor.: C=49.82%; H=5.41%; N=6.45%; P=4.75%; Cl=16.33%. Found: C=49.26%; H=5.07%; N=5.12%; P=3.50%; Cl=16.50%.

If a mixture of different alkaloids is mixed with Thio-TEPA, three molecules of different alkaloids may be bound to one Thio-TEPA molecule and thus a large number of components may be synthesized. In this very complex mixture of reaction products, one or more of the reaction products can be responsible for the unique biological activity. Actually, more than 50 points, fluorescent under UV-light resulted from the separation of the reaction products of Thio-TEPA and the alkaloid extract of *Chelidonium majus* L. by two-dimensional thin-layer chromatography. Furthermore, it could be proven that no free ethylene groups of the Thio-TEPA exist in the preparation of the reaction products produced from the alkaloid extract of *Chelidonium majus* L. reacted with Thio-TEPA. This proof based on chemical analysis, and biological tests to compare the lethal dose of Thio-TEPA which is 1 mg/kg body weight, whereas, a dose of 250 mg/kg body weight of the Thio-TEPA derivative(s) of the alkaloid extract of *Chelidonium majus* L. is not toxic. Moreover, the preparation has no effect on leukemia 1210 and none on the blood picture. It can be derived from this that the ethylene groups of Thio-TEPA, which are also responsible for its toxic effect, are blocked in the reaction with alkaloids.

It is significant for diagnostic purposes that the hydrochloride of the reaction product(s) of Thio-TEPA and the alkaloid extract of *Chelidonium majus* L. has the property of being yellow-green fluorescent in ultraviolet light. The excitation frequencies lie within the frequency range from 220 to 490 nm. The spectral width of the fluorescence extends from 410 nm to 665 nm, while the maximum lies at 550 nm. This large spectral width is explained by the fact that the preparation is composed of a group of different alkaloid derivatives. The visibility limit of the fluorescence phenomenon under UV 366 nm on the plate for thin-layer chromatography lies at a dilution of 0.000007 mg/ml, 0.0000003 mg per 1 mm$^2$. The preparation also maintains this property in the living body, and thus, the distribution of the preparation could be observed in clinical experiments.

Several clinical case studies are reported below. In each, the hydrochloride salt of the reaction product(s) of Thio-TEPA and the alkaloid extract of *Chelidonium majus* L. was employed as the preparation for treatment and/or diagnosis.

Case 1

Patient M.B., 64 years old, male; diagnosis: Adenocarcinoma of the rectum with extensive metastasis in the LWS-area. Os il. sin. and Femur dext.

Two treatments were carried out with the preparation. Doses were 140 mg and 160 mg.

Course: Improvement of the general state, slight use of analgesics. Subjective better condition, feeling of warmth in the tumor area rising and falling like waves.

Fluorescence factor: 6 days after completion of the 2nd treatment clearly demarcated fluorescence in the skin area over the tumor and its surrounding area. Also fluorescence in a limited clinical tumor-free skin area. These sites are identical with the areas perceived as warmer. The greater local heat development is objectivized by bands of fever. 13 days later, the fluorescence is much less intense appearing as irregular spotty patterns.

Case 2

Patient R.N., 68 years old, male; diagnosis: Bronchus-Ca li. Upper lobe. Histological: Large cell, infiltrative N. bronchi. Icterus, liver metastasis.

Three times diagnostic applications of the preparation. Total amount 130 mg. Strong fluorescence the size of a dinner plate appeared over the oxyphoid. Questionable fluorescence over the left thorax wall. One week later: No fluorescence can be established.

Case 3

Patient M.L., 72 years old, female; diagnosis: Pancreas carcinoma, numerous liver metastasis. Operation: Probatoria and P.E. from a liver metastasis. Historical: Metastasis of a polymorphous cell, practically mucous forming adenocarcinoma. Constant pain and extreme alkaloid consumption, Epidural catheter, instillation v. Carbestesin, splanchicus block. Ultrasound: Liver metastasis, large pancreas. A treatment with the preparation, interrupted by giving of placebo.

Palpatoric: Reduction in size of the left liver lobe from 5 to 3 transverse fingers under the rib case. Metastasis seems to have lessened.

After injection of the preparation, the leukocytes increased to 13000. Fluorescence present a few days after beginning of therapy, medial of the Op wound at one time 30 mm large fluorescence, was later not reproducible.

Case 4

Patient R.M., 73 years old, female, diagnosis: Inoperable stomach carcinoma. Operation: Probatoria and partial reticulum resection. On the evening before the operation, 2 individual doses of 20 mg of the preparation were administered by i.v.

Histological: Extensive lymph angiosis carcinomatosa of the large reticulum with adenocarcinoma of the stomach. Fluorescence factor: Strong fluorescence of the resec. reticulum part. N.B.: No fluorescence of the large reticulum in the case of the healthy patient. Nodes in the mamma (Cystic mastopathy) is not fluorescent after the preparation.

Case 5

Patient W.S., 26 years old, male; diagnosis: Scar keloid (over the xyphoid).

0.5 mg of the preparation in 1 ml 0.9% sodium chloride (physiological) solution were administered subcutaneously 50 cm removed from keloid (naval area); approximately one minute after the injection strong fluorescence of the keloid was detected continued for 2 days.

Case 6

Patient N.U., 58 years old, female, diagnosis: Mammary carcinoma. Histological: Carcinosis pleurea, multiple bone metastasis. Condition after recurring pleurae affusions, cytostatic-instillation.

2.5 mg of the preparation was injected. After a short time, fluorescence clear in the case of drain (4 RFI under OP scar) of pleurae effusion with slight fluorescence in the area of the mamma-amputation scar.

Summary of Clinical Results 60 patients have been treated with the preparation "Ukrain", which is a tradename for the hydrochloride salt of the reaction product(s) of thiophosphoric acid triaziridide (Thio-TEPA) and the alkaloid extract of the great celandine (*Chelidonium majus* L.). Further details of the preparation of this hydrochloride salt are found in my Austrian Pat. No. 354,644 granted Jan. 25, 1980, the entire disclosure of which is incorporated herein by reference. 59 of these patients were in an advanced stage of cancer.

In the course of clinical observation, it was revealed that the preparation influences tumor growth in different ways. In no case, does the preparation lead to a bone marrow depression worthy of mention.

The patients could be divided into three groups based on the stage of advancement of the disease. Group I includes 8 patients, 2 female patients with Mamma-Ca; 2 patients with malignant melanoma; 1 patient with basocellular epithelioma; 1 patient with recurrence of a cylinder cell carcinoma of the parotis; 2 patients with alleged mamma-carcinoma, one who did not agree to taking a weight specimen and the other one, on examination, suffering only multiple metastasis of an adenomacarcinoma appeared in the axillary and supraclavicular area, but in both the primary tumor could not be located. A clear remission of the tumor tissue was shown in all of the 8 cases, whereby the tumor tissue reformed partially in reverse sequence to its origin, that is to say, that those metastases which appeared last, were the first to disappear. No necrosis occurred; but next a clear demarcation of the tumor tissue appeared against the surrounding area with retrogression of the local swelling and eventually also of the existing lympho-edema with hindrance of drainage. Then, the tumor nodes slowly became smaller.

A clear effect in the form of subjective sensations was felt by these patients immediately after the first injection, such as:

Subsidal of the pain, in one case occurring 1-2 hours after the injection; feeling of warmth in the tumor, which with one patient was determined as local warming; tension and irritation in the tumor area, heat sensation, tachycardia, slight vertigo or headache; increased urine precipitation; fatigue, depression, nausea and partial depression. These symptoms did not occur at the same time; but with all patients some of the symptoms occurred in individual rhythm after each injection.

From the plots of these effects in one patient, variations in pulse, blood pressure and temperature values could be directly correlated to the occurrence of the named subjective phenomena.

Group III included 27 patients: 10 bronchial-Ca; 6 with Mamma-Ca; 2 with Ovarial-Ca; 2 with Uterus-Ca; 1 with pancreas-Ca; 2 with Rectum-Ca; 1 with stomach-Ca and one with abdominal tumor, which could not be clearly localized because of the progressed state of the primary tumor. In contrast to Group I, an effect was shown here with reference to the tumor as well as with reference to the described side effects. Even with longer treatment time and higher doses, no changes occurred which could be attributed to the preparation Ukrain.

Group II was, so-to-speak an intermediate group and consisted of 25 patients in extremely advanced state of illness: 9 with Mamma-Ca; 7 with bronchial-Ca; rectum-Ca; 2 with osteosarcoma; 1 with prostate-Ca; 1 with thyroid-Ca; 1 with colon-Ca; 1 with stomach-Ca and 1 with abdominal tumor. The effect of the preparation was very different here. With all these patients, the accompanying symptoms occurred as described in Group I patients, but not so rapidly, after extended treatment.

With these patients, the effect of the preparation on the tumor was not so clearly manifested which may be attributed to the fact that the cancer growth was very advanced. In the case of 2 patients with bronchial-Ca, a short remission of the tumor occurred. In 2 patients, a temporary cessation of growth resulted. In the case of 4 patients with Mamma-Ca, healing of the ulcerations over the metastasis resulted. In the case of other patients, regression of the tumor-caused pain, and partial freedom from pain was attributable to administration of Ukrain. In the case of one female patient with a diffuse infiltrating thyroid gland carcinoma recurrence, the tumor changed in such a way that it could be easily distinguished from the healthy tissue. With almost all these patients, the general condition improved notwithstanding prognosis, even if the tumor growth could not be stopped.

For a better understanding of the description of the foregoing case studies, a representative case of a patient from each group is reported below.

A Group I Patient

Patient T.J., female, 40 years old, diagnosis: Malignant melanoma. Histologically verified. (In 1977 a malignant melanoma on the left leg verified and operated on.)

In 1980, a lymph node metastasis was found in the left groin, having a size of 5×5 cm. The patient was treated with Ukrain. In the course of a three-part treatment, she received a total of 680 mg.

During the first treatment she sustained temporary depression, muscle pain and generally poor feeling, as well as an increase in lymph node metastasis lasting 10 days. After the second treatment the lymph node was only the size of a walnut and after the third treatment it was the size of a bean. It was hard and not well palpable. Her general condition was good.

A Group II Patient

Patient H.G., female, 63 years old, diagnosis: Mamma carcinoma on the left side with supraclavicular lymph node metastasis and bone metastasis.

Prior systematic therapy carried out: Nolvadex from June 1977 to January 1978; Polychemotherapy with Endoxan, Methotrexate, Flour-Uracil and Prednisolone, later combination therapy with Adriblastin-Endoxan from March 1978 to April 1979. Elipten (Aminoglytethimide) from April 1979 to January 1980. Therapy with Ukrain began on Feb. 29, 1980.

At the beginning of therapy, a 5×5 cm large ulcerated supraclavicular metastasis was found. Subjective feeling of pressure in the area of the eye as well as feeling of stress in the left supraclavicular were recorded. The therapy was begun with 2.5 mg. Right at the beginning of the therapy, the patient noticed a feeling of warmth in the area of the left side of the body, and under the supraclavicular tumor. This feeling of warmth did not reoccur. No more ulcerations were visible in the left supraclavicular after 6 injections. However, the tumor itself was unchanged. Stressful feelings and the feeling of pressure in the area of the eyes that existed for two years disappeared. During the last check on Apr. 8, 1980, the patient was free of such subjective complaints. She complained of moderate weight loss. Local li. supraclavicular was unchanged. No ulcerations could be proven at that time. No pathological laboratory findings (blood picture, SMA, serum calcium) could be recorded. No worsening side effects could be determined.

A Group III Patient

Patient K.G., female, 58 years old, diagnosis: Adeno-solid ovarian carcinoma, operatively removed.

Prior systematic therapy carried out: Endoxan 1200 mg per infusions. Cobalt radiation 4500 rd/g.

Prophylactic therapy with Ukrain was undertaken. No side effects or subjective perceptions during the treatment such as vertigo, temperature increase, tachycardia or depression were experienced. The patient's general feeling, condition, and appetite improved. On month after the beginning of the therapy a node was found in the left breast; and one week later a mammectomy was carried out according to Patey. The histology showed a partially necroticized solid carcinoma. The treatment with Ukrain was discontinued.

To determine the effect of the mechanism of therapeutic and diagnostic capacity of Ukrain, studies were carried out concerning the immuno-stimulating effect of Ukrain in vitro in the so-called lymphocyte-transformation test, and results of the studies are reported in the following tables. Generally, lymphocytes are known to be immunocompetent when they are capable of recognizing the specific antigen, or if they are capable of reacting with it. Such cells are called immunocytes and their successors are called immunoblasts.

The formation of immunoblasts can also be carried out in vitro. The immunoblasts have a size of 20–30μ, whereas, normal lymphocytes have a size of only 5–15μ. In the following immunological tests, isolated lymphocytes of healthy humans and of guinea pigs were used for the blast transformation after the addition of Ukrain. A mixture of the compound known under the tradename Ficoll 4000 and EDTA was used for the isolation (0.9 EDTA+0.1 Ficoll 4000).

The isolated lymphocytes were grown in vitro in Parker solution, with an addition of 1.6 μg, 0.16 μg and 0.016 g. At the same time lymphocytes were bred in Parker solution with 5 μg/ml of the unspecific stimulator phytohemaglutinin (PHA) and without an additive as a control run. In order to avoid colonization of bacteria, effective amounts of antibiotics, penicillin, streptomycin and nystatin, were added. The cultures were incubated at 37° C. and the number of transformed lymphocytes was counted daily under the microscope for 3 days.

100 lymphocytes were counted out in each preparation and those lymphocytes which were larger than 15μ (from humans) and larger than 20μ in the case of guinea pigs were evaluated as being transformed. In all cases, before the beginning of breeding, the number of transformed cells was not larger than 10.1%. The tests were carried out with the lymphocytes of 10 healthy humans and 10 healthy guinea pigs.

Since in the case of a cure with Ukrain the average single dose amounts to 10 mg (the mean individual dose of Ukrain used in these experiments being 16 mg), the dose of Ukrain was actually 1/10000; 1/100000 and 1/1000000 of the amount. The results are summarized in the following Tables I and II:

TABLE I

| | Percentage of transformed guinea pigs lymphocytes. | | | |
|---|---|---|---|---|
| | Culture-medium | Breeding Time | | |
| No. | With Additive | 24 hrs. | 48 hrs. | 72 hrs. |
| 1. | 1.6* | 48.6 | 45.6 | 40.2 |
| | 0.16* | 42.3 | 29.3 | 28.5 |
| | 0.016* | 35.6 | 33.6 | 25.0 |
| | PHA | 32.2 | 28.3 | 27.9 |
| | Without stimulator | 19.2 | 15.3 | 1.8 |
| 2. | 1.6* | 53.9 | 30.2 | 18.3 |
| | 0.16* | 48.7 | 32.2 | 32.0 (?) |
| | 0.016* | 27.3 | 30.2 | 18.5 |
| | PHA | 20.8 | 17.2 | 17.5 |
| | Without stimulator | 13.3 | 12.2 | 19.2 (?) |
| 3. | 1.6* | 50.2 | 48.3 | 42.8 |
| | 0.16* | 49.3 | 51.1 | 39.9 |
| | 0.016* | 41.0 | 29.3 | 30.1 |
| | PHA | 32.5 | 29.8 | 22.3 |
| | Without stimulator | 18.0 | 11.2 | 10.3 |
| 4. | 1.6* | 55.6 | 42.3 | |
| | 0.16* | 50.8 | 40.7 | 43.8 |
| | 0.016* | 41.2 | 38.5 | 39.5 |
| | PHA | 33.2 | 27.0 | 18.0 |
| | Without stimulator | 18.2 | 18.0 | 16.2 |
| 5. | 1.6* | 51.3 | 43.5 | 31.5 |
| | 0.16* | 48.2 | 33.2 | 33.5 |
| | 0.016* | 39.9 | 31.5 | 30.2 |
| | PHA | 33.4 | 20.3 | 11.3 |
| | Without stimulator | 12.5 | 12.5 | 8.4 |
| 6. | 1.6* | 58.5 | 57.9 | 41.8 |
| | 0.16* | 48.3 | 50.0 | 43.2 |
| | 0.016* | 40.1 | 35.2 | 30.0 |
| | PHA | 30.2 | 22.1 | 17.3 |
| | Without stimulator | 19.0 | 18.2 | 13.5 |
| 7. | 1.6* | 43.3 | 41.2 | 39.8 |
| | 0.16* | 42.3 | 36.6 | 36.2 |
| | 0.016* | 41.2 | 37.2 | 35.5 |
| | PHA | 33.3 | 33.4 | 27.2 |
| | Without stimulator | 15.1 | 16.1 | 13.2 |
| 8. | 1.6* | 48.7 | 45.1 | 40.3 |
| | 0.16* | 43.1 | 39.2 | 31.1 |
| | 0.016* | 35.6 | 29.8 | 24.2 |
| | PHA | 31.3 | 27.0 | 24.3 |
| | Without stimulator | 12.2 | 10.1 | 10.5 |
| 9. | 1.6* | 53.3 | 51.5 | 41.2 |
| | 0.16* | 49.6 | 47.2 | 42.2 |
| | 0.016* | 39.2 | 36.7 | 34.6 |
| | PHA | 38.3 | 32.8 | 25.2 |
| | Without stimulator | 18.1 | 16.7 | 11.3 |
| 10. | 1.6* | 56.2 | 53.6 | 40.7 |
| | 0.16* | 49.3 | 42.8 | 34.5 |
| | 0.016* | 39.8 | 37.3 | 28.3 |
| | PHA | 34.2 | 33.2 | 27.5 |
| | Without stimulator | 12.0 | 10.2 | 8.4 |

*Amount of Ukrain in units of μg/ml.

TABLE II

| | Percentage of transformed human lymphocytes. | | | |
|---|---|---|---|---|
| | Culture-medium | Breeding Time | | |
| No. | With Additive | 24 hrs. | 48 hrs. | 72 hrs. |
| 1. | 1.6* | 47.2 | 43.4 | 41.2 |
| | 0.16* | 43.8 | 39.2 | 38.6 |
| | 0.016* | 39.6 | 36.7 | 35.2 |
| | PHA 5 μg/ml | 36.6 | 24.8 | 20.8 |
| | Without stimulator | 11.1 | 9.2 | 9.0 |
| 2. | 1.6* | 49.9 | 41.2 | 37.2 |
| | 0.16* | 43.2 | 40.3 | 33.2 |
| | 0.016* | 38.6 | 36.2 | 26.8 |
| | PHA 5 μg/ml | 31.2 | 28.0 | 21.2 |
| | Without stimulator | 18.4 | 14.1 | 8.4 |
| 3. | 1.6* | 19.1 | 18.8 | 16.2 |
| | 0.16* | 19.5 | 18.2 | 15.3 |
| | 0.016* | 14.2 | 15.3 | 13.2 |
| | PHA 5 μg/ml | 33.1 | 28.2 | 14.1 |
| | Without | 10.7 | 9.3 | 15.3 |

TABLE II-continued

Percentage of transformed human lymphocytes.

| No. | Culture-medium With Additive | Breeding Time 24 hrs. | 48 hrs. | 72 hrs. |
|---|---|---|---|---|
| 4. | 1.6* | 43.9 | 42.8 | 39.4 |
| | 0.16* | 41.2 | 40.6 | 41.2 |
| | 0.016* | 33.6 | 32.1 | 31.2 |
| | PHA 5 µg/ml | 40.2 | 33.6 | 28.3 |
| | Without stimulator | 13.6 | 12.3 | 10.8 |
| 5. | 1.6* | 53.3 | 51.5 | 47.8 |
| | 0.16* | 48.6 | 43.6 | 41.0 |
| | 0.016* | 37.2 | 37.8 | 36.2 |
| | PHA 5 µg/ml | 36.4 | 28.5 | 25.4 |
| | Without stimulator | 15.3 | 14.4 | 12.8 |
| 6. | 1.6* | 55.5 | 53.4 | 51.5 |
| | 0.16* | 51.2 | 49.1 | 47.3 |
| | 0.016* | 43.2 | 36.2 | 36.0 |
| | PHA 5 µg/ml | 37.1 | 36.2 | 34.7 |
| | Without stimulator | 19.3 | 18.4 | 16.5 |
| 7. | 1.6* | 48.6 | 46.8 | 42.5 |
| | 0.16* | 47.2 | 45.2 | 24.3 |
| | 0.016* | 39.8 | 32.0 | 21.2 |
| | PHA 5 µg/ml | 30.1 | 26.8 | 19.0 |
| | Without stimulator | 14.7 | 13.1 | 8.5 |
| 8. | 1.6* | 52.3 | 37.4 | 21.8 |
| | 0.16* | 48.3 | 28.3 | 19.3 |
| | 0.016* | 41.2 | 19.4 | 17.4 |
| | PHA 5 µg/ml | 37.3 | 19.5 | 20.1 |
| | Without stimulator | 9.0 | 8.3 | 8.2 |
| 9. | 1.6* | 47.2 | 32.8 | 29.1 |
| | 0.16* | 43.4 | 36.4 | 34.2 |
| | 0.016* | 38.6 | 25.0 | 20.0 |
| | PHA 5 µg/ml | 36.6 | 28.6 | 21.4 |
| | Without stimulator | 15.3 | 13.3 | 10.7 |
| 10. | 1.6* | 48.3 | 37.4 | 33.3 |
| | 0.16* | 43.4 | 41.2 | 36.8 |
| | 0.016* | 37.1 | 36.2 | 29.1 |
| | PHA 5 µg/ml | 30.0 | 19.4 | 18.4 |
| | Without stimulator | 9.3 | 9.6 | 5.3 |

*Amount of Ukrain in units of µg/ml.

In the test a statistically significant difference was shown between the number of transformed lymphocytes of humans and of animals and of control groups absent Ukrain. The conclusion can be drawn from this that the preparation Ukrain has an immunological effectiveness and stimulates the human defense mechanism. Clear transformation of lymphocytes did not occur in only one out of 10 cases (see Table II, No. 3, where human lymphocytes were tested. In the case of patient no. 3, under certain circumstances as "in vitro equivalent" could exist for the clinical phenomenon, in which individual patients showed no reaction at all to Ukrain).

Although no clear lymphocytes transformation was effected by Ukrain in the case of test person no. 3, a higher lymphocyte transformation was obtained with all other patients than with PHA.

Finally, the conventional Agargel electrophoresis using 0.05 mg Ukrain, was run on Agargel (Corensen buffer+NaCl) and was put into a small notch and lasted 4 hours at 70 volts and 2 mA, a filter paper was pressed on the surface, the start and the polarity were marked; a fluorescent band directed to a negative pole was defected under UV-lamp. The fluorescent fractions were positively charged.

It is apparent from the preceding that the subject preparations or compounds described at the beginning of this specification can be used for diagnosing as well as for the therapeutic treatment of tumors of all types, and also for diagnosing and treating infectious diseases. According to the invention, the fluorescent effect of the Ukrain preparations is of great significance. For diagnosis, it is thus possible for rapid early detection, after the injection of the preparation(s), by virtue of its accumulation in the diseased tissue area. Rapid and reliable diagnosis can be based on that accumulation by observing decomposition and the rate of decomposition of the injection fluid in the injected area and/or by observing the localization of same in the diseased area, for example, in the tumor tissue. This observation extends to all endoscopic methods including bronchoscopy, mediastinoscopy, thorascopy, esophagoscopy, Otorhinoscopy, laryngoscopy, rectoscopy, proctoscopy among others, where for example, cold light is replaced by UV-light.

In this connection, the preparation may be radioactively labelled with radioactive isotopes, and then the diagnostic method includes measuring radioactivity of the accumulated radioactively labelled preparation in a known manner with suitable detectors; and accumulation can be recorded for example with gamma-ray scanners. In addition to labelling of the described preparations with fluorescent materials and radioactive isotopes, the preparations may be doped with radiation-absorbing compounds or radicals, so that accumulation of the doped preparation may be detected in a certain tissue area due to the increased absorption of X-radiation there.

It is especially noteworthy in this connection that in the case of very many patients, infections disappeared after the first Ukrain injection. Among them were stubborn mycosis which previously had not responded to any therapy, cases of chronic bronchitis and throat inflammations of unclear genesis, as well as other viral and bacterial diseases, according to the treating physicians. Thus, the previous results also suggest the stimulation of lymphocytes to immunocytes by means of the preparation; such stimulation is equivalent to the production of the so-called killer-cells which destroy the affected tissue or the tissue foreign to the body, or virus which has penetrated healthy cells, and/or bacteria, fungi, and the like. Therefore, the healing of tumor diseases, as well as viral diseases, bacterial diseases and fungal diseases, and in addition a healing of polyarthritis can be realized.

What is claimed is:

1. A method for treating a human patient having tumor cells located in the rectum, liver, pancreas, stomach, skin, glands, lymphatic system, bone, parotid gland, ovaries, uterus, lungs, prostate, thyroid, abdomen or colon comprising administering to said patient a mixture of non-toxic cytostatic alkaloid derivatives in an amount of from about 0.5 mg to 650 mg, wherein at least a portion of said mixture of alkaloid derivatives is comprised of derivatives of chelilutin so as to at least retard the growth of said tumor cells.

2. The method of claim 1 whereby said tumor cells are destroyed by administration of said mixture of cytostatic alkaloid derivatives comprising derivatives of chelilutin.

3. The method of claim 1 whereby at least a major portion of said cytostatic alkaloid derivatives are present in said mixture as water soluble salts.

4. The method of claim 1 whereby said mixture of alkaloid derivatives is administered intravenously.

5. The method of claim 1 whereby said mixture of alkaloid derivatives is administered by injection.

6. The method of claim 1 whereby said alkaloid derivatives are formed from an alkaloid extract of *Chelidonium majus* L.

7. The method of claim 1 wherein said chelilutin derivative is a chelilutin thiophosphoric acid amide salt.

8. The method of claim 7 wherein said thiophosphoric acid is selected from the group consisting of thiophosphoric acid triaziridide, thiophosphoric acid-tri-(N-sanguinarinol)-ethylamine, thiophosphoric acid-di-(ethyleneimido)-N-herberinol-ethylamide and N,N$^1$,N$^{11}$-triethylene-thiophosphoramide.

9. The method of claim 8 wherein said thiophosphoric acid is thiophosphoric acid triaziridide.

* * * * *

UNITED STATES PATENT AND TRADEMARK OFFICE
CERTIFICATE OF CORRECTION

PATENT NO. : 4,816,462
DATED : March 28, 1989
INVENTOR(S) : Wassyl Nowicky

It is certified that error appears in the above-identified patent and that said Letters Patent is hereby corrected as shown below:

Column 1, Line 34, "doesnot" should read -- does not --.

Column 2, Line 18, "quinarine" should read -- guinarine --.

Column 7, Line 32, "-cH$_2$-" should read -- -CH$_2$- --.

Column 7, Line 55, "N" (second occurrence) should read -- n --.

Column 8, Line 8, "-CH$_2$-CH$_2$- or -CH2-CH$_2$-CH$_2$" should read -- -CH$_2$-CH$_2$- or -CH$_2$-CH$_2$-CH$_2$ --.

Column 8, Line 47, "(gas" should read -- gas --.

Column 9, Line 35, "H = 5.56S%;" should read -- H = 5.56%; --.

Column 9, Line 54, "=" should read -- + --.

Column 10, Line 39, "P=2.96;" should read -- P=2.96%; --.

Column 10, Line 41, "P=2.27;" should read -- P=2.27%; --.

UNITED STATES PATENT AND TRADEMARK OFFICE
CERTIFICATE OF CORRECTION

PATENT NO. : 4,816,462
DATED : March 28, 1989
INVENTOR(S) : Wassyl Nowicky

It is certified that error appears in the above-identified patent and that said Letters Patent is hereby corrected as shown below:

Column 10, Line 51, "bis" should read -- Bis --.

Column 15, Line 7, "On" should read -- One --.

Signed and Sealed this

Fourteenth Day of January, 1992

Attest:

HARRY F. MANBECK, JR.

*Attesting Officer*  *Commissioner of Patents and Trademarks*